United States Patent
Minor et al.

(10) Patent No.: US 6,932,918 B2
(45) Date of Patent: Aug. 23, 2005

(54) AZEOTROPE-LIKE COMPOSITIONS CONTAINING FLUOROETHANE

(75) Inventors: Barbara Haviland Minor, Elkton, MD (US); Vinci Martinez Felix, Kennett Square, PA (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/420,368

(22) Filed: Apr. 22, 2003

(65) Prior Publication Data

US 2003/0199408 A1 Oct. 23, 2003

Related U.S. Application Data

(62) Division of application No. 09/901,239, filed on Jul. 9, 2001, now Pat. No. 6,641,752, which is a division of application No. 08/943,420, filed on Oct. 3, 1997, now Pat. No. 6,261,472.
(60) Provisional application No. 60/029,971, filed on Nov. 4, 1996.

(51) Int. Cl.$^7$ ................................................. C09K 5/04
(52) U.S. Cl. ........................................ 252/67; 521/114
(58) Field of Search .............................. 252/67; 516/8; 521/114, 117

(56) References Cited

U.S. PATENT DOCUMENTS

| | | | |
|---|---|---|---|
| 3,991,094 A | * 11/1976 | Zanker | ....................... 560/348 |
| 4,226,976 A | * 10/1980 | Goodman et al. | ........... 528/498 |
| 5,248,433 A | 9/1993 | Felix et al. | .................... 252/67 |
| 5,417,871 A | 5/1995 | Minor et al. | ................... 252/67 |
| 5,441,659 A | 8/1995 | Minor | ........................... 252/67 |
| 5,814,674 A | * 9/1998 | Pauls et al. | .................... 521/49 |

FOREIGN PATENT DOCUMENTS

| | | |
|---|---|---|
| GB | 2 298 866 A | 9/1996 |
| JP | 53062789 | 6/1975 |
| WO | WO 92/01762 | 2/1992 |
| WO | WO 92/11338 | 7/1992 |
| WO | WO 92/19393 | * 11/1992 |

* cited by examiner

*Primary Examiner*—John R. Hardee
(74) *Attorney, Agent, or Firm*—Mark A. Edwards; Chyrrea J. Sebree

(57) ABSTRACT

The present invention relates to the discovery of compositions which include fluoroethane, 2-fluoropropane or tert-butylfluoride. These compositions are useful as pure components or with at least one of tetrafluoroethane, difluoroethane, hexafluoropropane, a hydrocarbon or dimethylether.

These compositions are useful as aerosol propellants, refrigerants, cleaning agents, expansion agents for polyolefins and polyurethanes, refrigerants, heat transfer media, gaseous dielectrics, fire extinguishing agents, power cycle working fluids, polymerization media, particulate removal fluids, carrier fluids, buffing abrasive agents, and displacement drying agents.

2 Claims, 21 Drawing Sheets

AZEOTROPE-LIKE COMPOSITIONS CONTAINING FLUOROETHANE

CROSS-REFERENCE TO RELATED APPLICATION

This application claims the benefit of U.S. Provisional Application. No. 60/029,971, filed Nov. 4, 1996 and is a divisional of U.S. application Ser. No. 09/901,239, now U.S. Pat. No. 6,641,752, filed Jul. 9, 2001, which is a divisional of U.S. application Ser. No. 08/943,420, now U.S. Pat. No. 6,261,472, filed Oct. 3, 1997.

FIELD OF THE INVENTION

The present invention relates to the discovery of compositions which include fluoroethane, 2-fluoropropane or tert-butylfluoride. These compositions are useful as pure components or with at least one of tetrafluoroethane, difluoroethane, hexafluoropropane, a hydrocarbon or dimethylether.

These compositions are useful as aerosol propellants, refrigerants, cleaning agents, expansion agents for polyolefins and polyurethanes, refrigerants, heat transfer media, gaseous dielectrics, fire extinguishing agents, power cycle working fluids, polymerization media, particulate removal fluids, carrier fluids, buffing abrasive agents, and displacement drying agents.

BACKGROUND OF THE INVENTION

Fluorinated hydrocarbons have had many uses, such as aerosol propellants, blowing agents and refrigerants. These compounds include trichlorofluoromethane (CFC-11), dichlorodifluoromethane (CFC-12) and chlorodifluoromethane (HCFC-22).

In recent years it has been pointed out that certain kinds of fluorinated hydrocarbons released into the atmosphere may adversely affect the stratospheric ozone layer. Although this proposition has not yet been completely established, there is a movement toward the control of the use and the production of certain chlorofluorocarbons (CFCs) and hydrochlorofluorocarbons (HCFCs) under an international agreement.

There is also a demand for aerosol propellants and blowing agents which have significantly less photochemical reactivity than hydrocarbons that contribute to the formation of ambient ozone and ground level smog. These compounds are typically referred to as low-VOC (volatile organic compound) or non-VOC.

Accordingly, there is a demand for the development of refrigerants that have a lower ozone depletion potential than existing refrigerants while still achieving an acceptable performance in refrigeration applications. Hydrofluorocarbons (HFCs) have been suggested as replacements for CFCs and HCFCs since HFCs have no chlorine and therefore have zero ozone depletion potential.

In refrigeration applications, a refrigerant is often lost during operation through leaks in shaft seals, hose connections, soldered joints and broken lines. In addition, the refrigerant may be released to the atmosphere during maintenance procedures on refrigeration equipment. If the refrigerant is not a pure component or an azeotropic or azeotrope-like composition, the refrigerant composition may change when leaked or discharged to the atmosphere from the refrigeration equipment. The change in refrigerant composition may cause the refrigerant to become flammable or to have poor refrigeration performance.

Accordingly, it is desirable to use as a refrigerant a single fluorinated hydrocarbon or an azeotropic or azeotrope-like composition that includes one or more fluorinated hydrocarbons.

Fluorinated hydrocarbons which are classified as low or non-VOC are also useful as aerosol propellants or blowing agents because they do not contribute significantly to ground level pollution.

Fluorinated hydrocarbons may also be used as cleaning agents or solvent to clean, for example, electronic circuit boards. It is desirable that the cleaning agents be azeotropic or azeotrope-like because in vapor degreasing operations the cleaning agent is generally redistilled and reused for final rinse cleaning.

Azeotropic or azeotrope-like compositions that include a fluorinated hydrocarbon are also useful as blowing agents in the manufacture of closed-cell polyurethane, phenolic and thermoplastic foams, as heat transfer media, gaseous dielectrics, fire extinguishing agents or power cycle working fluids such as for heat pumps. These compositions may also be used as inert media for polymerization reactions, fluids for removing particulates from metal surfaces, as carrier fluids that may be used, for example, to place a fine film of lubricant on metal parts or as buffing abrasive agents to remove buffing abrasive compounds from polished surfaces such as metal. They are also used as displacement drying agents for removing water, such as from jewelry or metal parts, as resist developers in conventional circuit manufacturing techniques including chlorine-type developing agents, or as strippers for photoresists when used with, for example, a chlorohydrocarbon such as 1,1,1-trichloroethane or trichloroethylene.

SUMMARY OF THE INVENTION

The present invention relates to the discovery of compositions which include fluoroethane, 2-fluoropropane or tert-butylfluoride. These compositions have zero ozone depletion potential (ODP), low global warming potential and are lower VOC than hydrocarbons. These compositions are also useful as pure components or with at least one of tetrafluoroethane, difluoroethane, hexafluoropropane, a hydrocarbon or dimethylether. These compositions are used as aerosol propellants, refrigerants, cleaning agents, expansion agents for polyolefins and polyurethanes, heat transfer media, gaseous dielectrics, fire extinguishing agents, power cycle working fluids, polymerization media, particulate removal fluids, carrier fluids, buffing abrasive agents, and displacement drying agents.

Further, the invention relates to the discovery of binary azeotropic or azeotrope-like compositions comprising effective amounts of fluoroethane, 2-fluoropropane or tert-butylfluoride and a second component of tetrafluoroethane, difluoroethane, hexafluoropropane, a hydrocarbon or dimethylether, to form an azeotropic or azeotrope-like composition. Azeotropes are highly desirable for refrigerants but not necessary for aerosol propellants.

The compounds of the present invention include the following components:

1. fluoroethane (HFC-161, or $CH_3CH_2F$, boiling point=−38° C.),
2. 1,1,2,2-tetrafluoroethane (HFC-134, or $CHF_2CHF_2$, boiling point=−20° C.),
3. 1,1,1,2-tetrafluoroethane (HFC-134a, or $CF_3CH_2F$, boiling point=−26° C.),
4. 1,1-difluoroethane (HFC-152a, or $CH_3CHF_2$, boiling point=−25° C.), 5. 2-fluoropropane (HFC-281ea, or $CH_3CHFCH_3$, boiling point=−11° C.),
6. tert-butylfluoride (HFC-3-10-1sy, or $(CH_3)_3CF$, boiling point=12° C.),
7. 1,1,1,2,3,3-hexafluoropropane (HFC-236ea, or $CF_3CHFCHF_2$, boiling point=6° C.),
8. 1,1,1,3,3,3-hexafluoropropane (HFC-236fa, or $CF_3CH_2CF_3$, boiling point=−1° C.),
9. dimethylether (DME, or $CH_3OCH_3$, boiling point=−25° C.),
10. butane ($CH_3CH_2CH_2CH_3$, boiling point=−0.5° C.),
11. isobutane (($CH_3)_3CH$, boiling point=−12° C.),
12. propane ($CH_3CH_2CH_3$, boiling point=−42° C.).

HFC-161 (CAS Reg. No. 353-36-6) and HFC-281ea (isopropyl fluoride, CAS Reg. No. 420-26-8) have been prepared by reaction of hydrogen fluoride with ethylene and propylene, respectively, as reported by Grosse and Lin in J. Org. Chem., Vol. 3, pp. 26–32 (1938).

2-Fluoro-2-methylpropane (t-butyl fluoride, HFC-3-10-1y, CAS Reg. No. [353-61-7]) may be prepared by the reaction of t-butyl alcohol with aqueous hydrogen fluoride as discussed on page 689 of "Chemistry of Organic Fluorine Compounds" by Milos Hudlicky, 2nd. ed., 1976.

DETAILED DESCRIPTION

Figure 1:
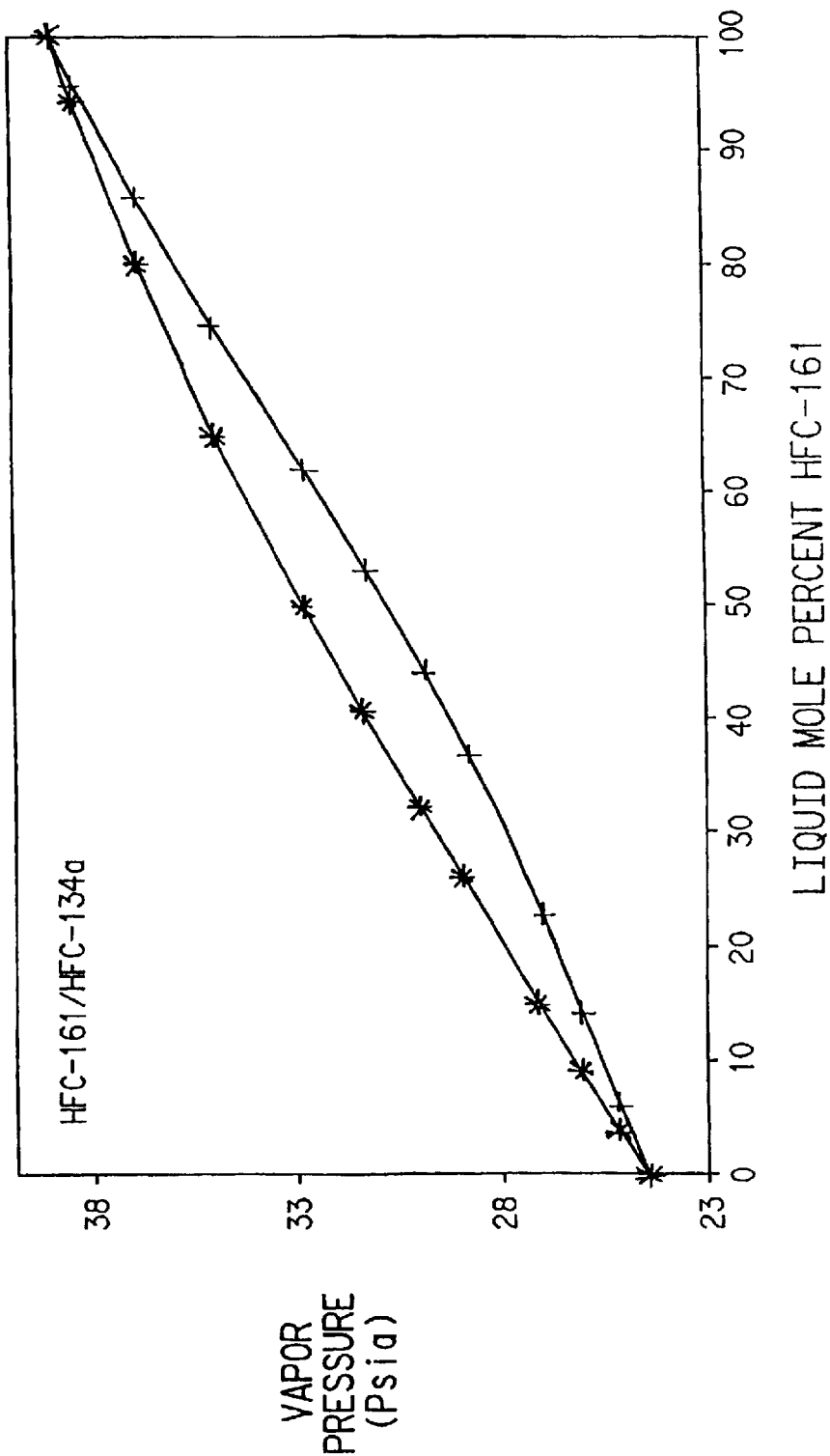
FIG. 1 is a graph of the vapor/liquid equilibrium curve for mixtures of HFC-161/HFC-134a at −14.15° C.
Figure 2:
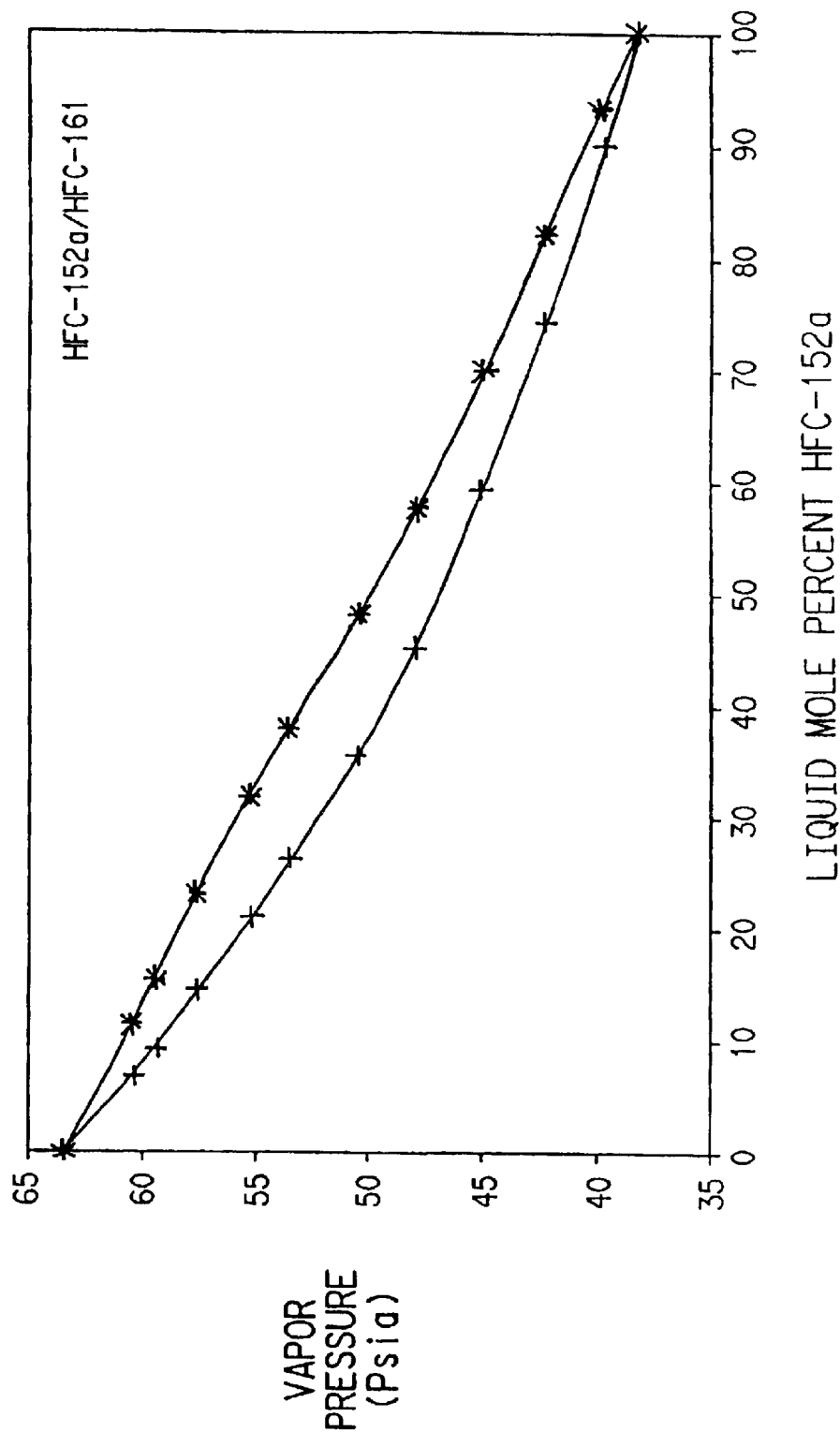
FIG. 2 is a graph of the vapor/liquid equilibrium curve for mixtures of HFC-161/HFC-152a at −0.05° C.
Figure 3:
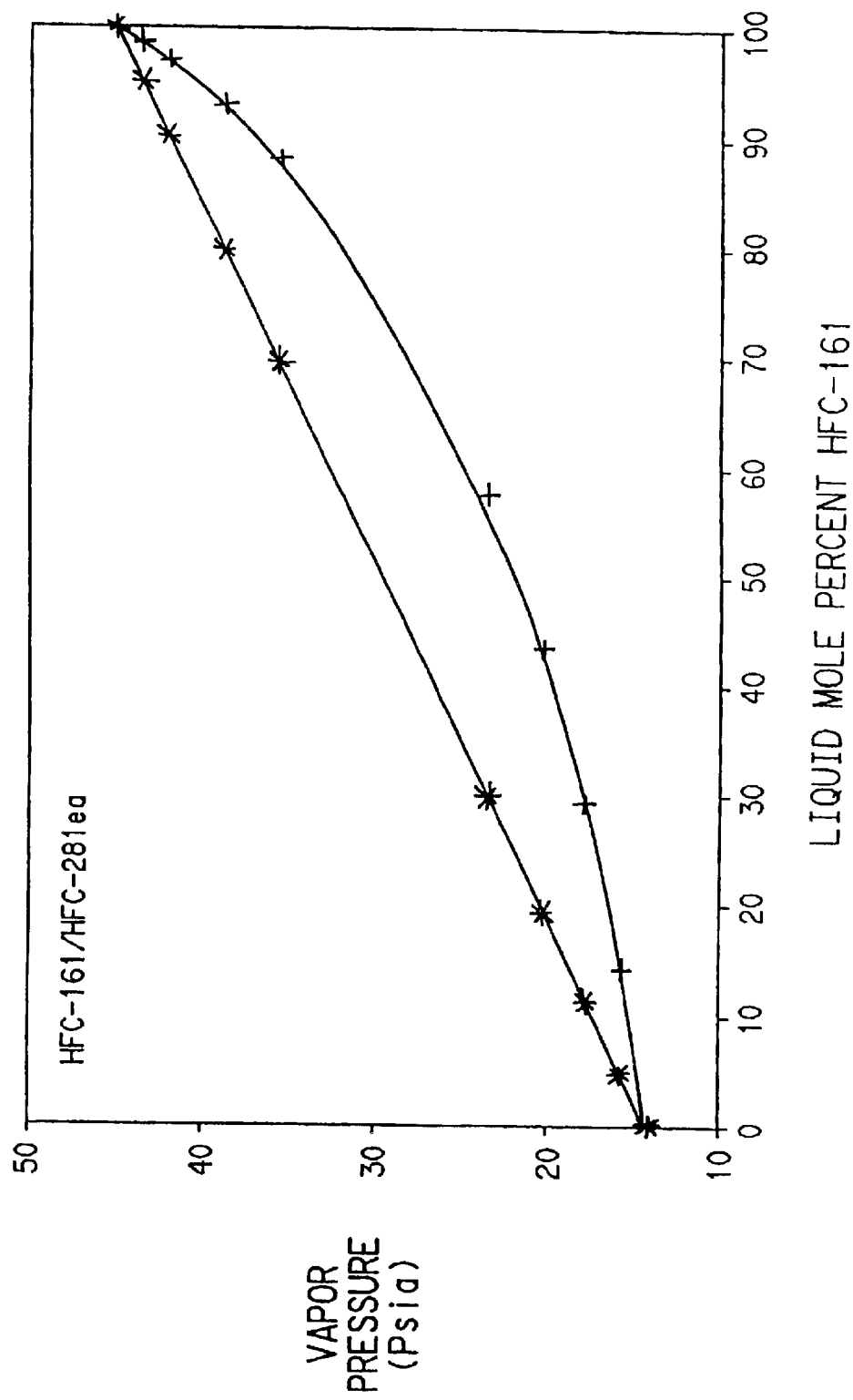
FIG. 3 is a graph of the vapor/liquid equilibrium curve for mixtures of HFC-161/HFC-281ea at −10° C.
Figure 4:
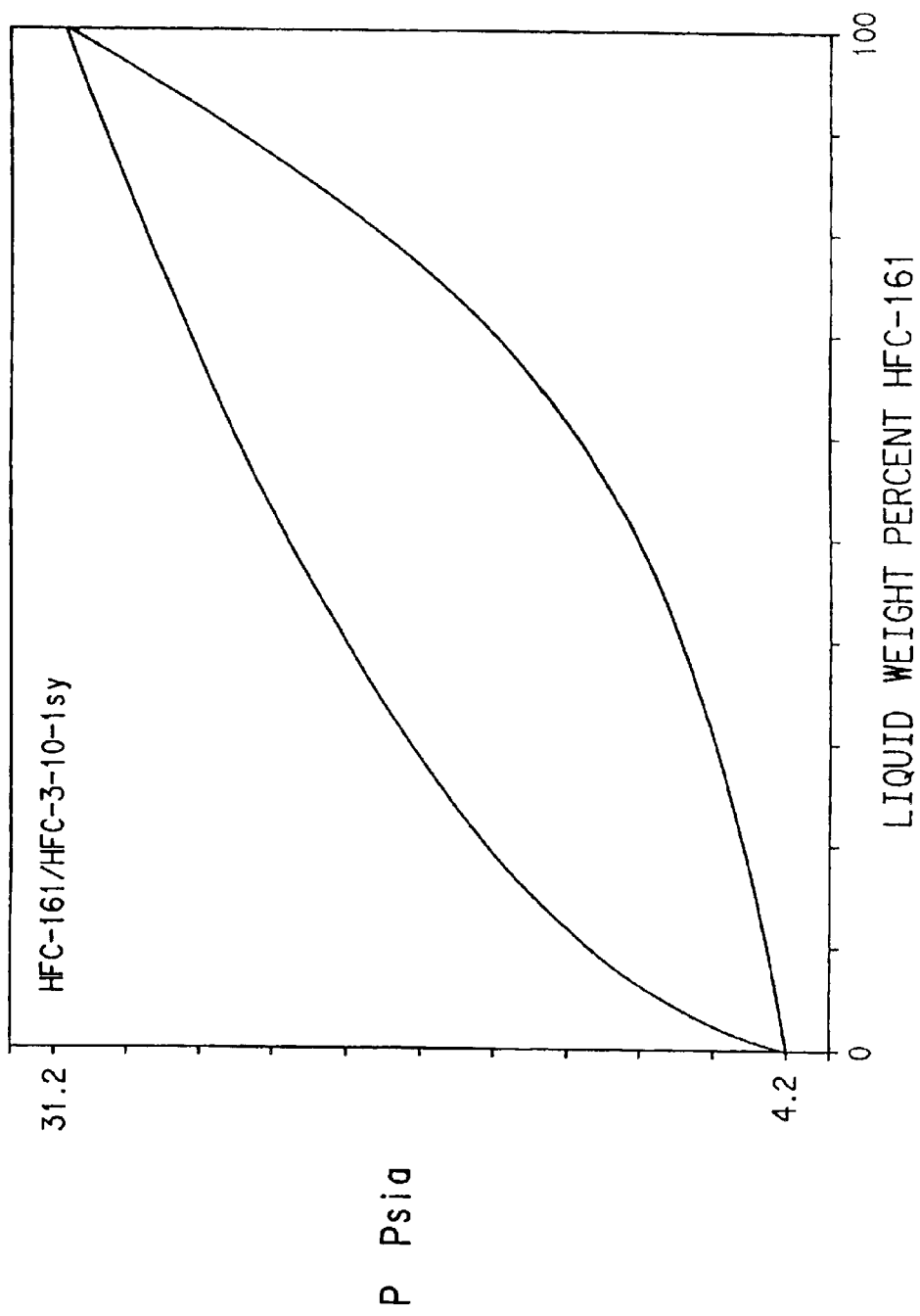
FIG. 4 is a graph of the vapor/liquid equilibrium curve for mixtures of HFC-161/HFC-3-10-1sy at −20° C.
Figure 5:
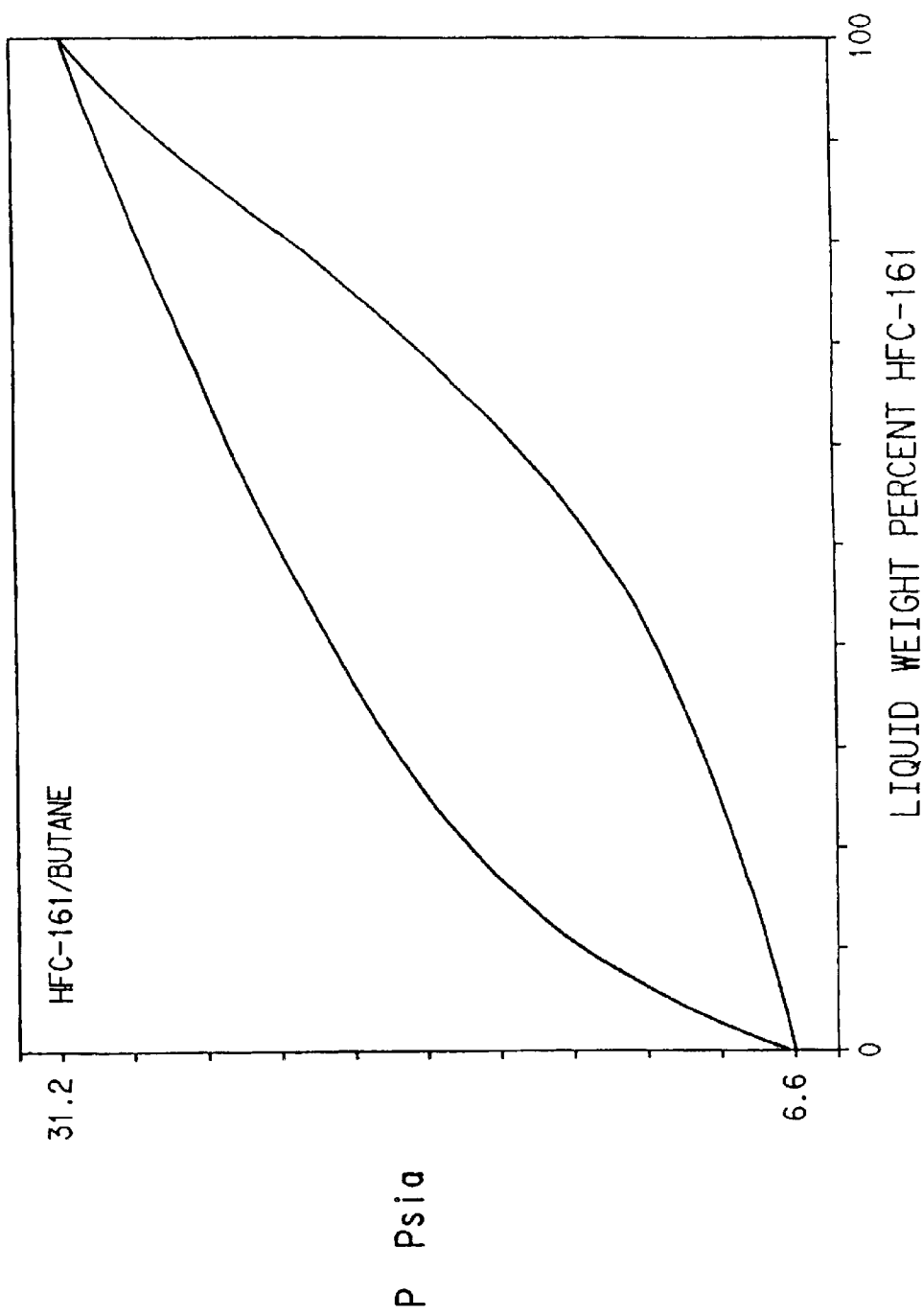
FIG. 5 is a graph of the vapor/liquid equilibrium curve for mixtures of HFC-161/butane at −20° C.
Figure 6:
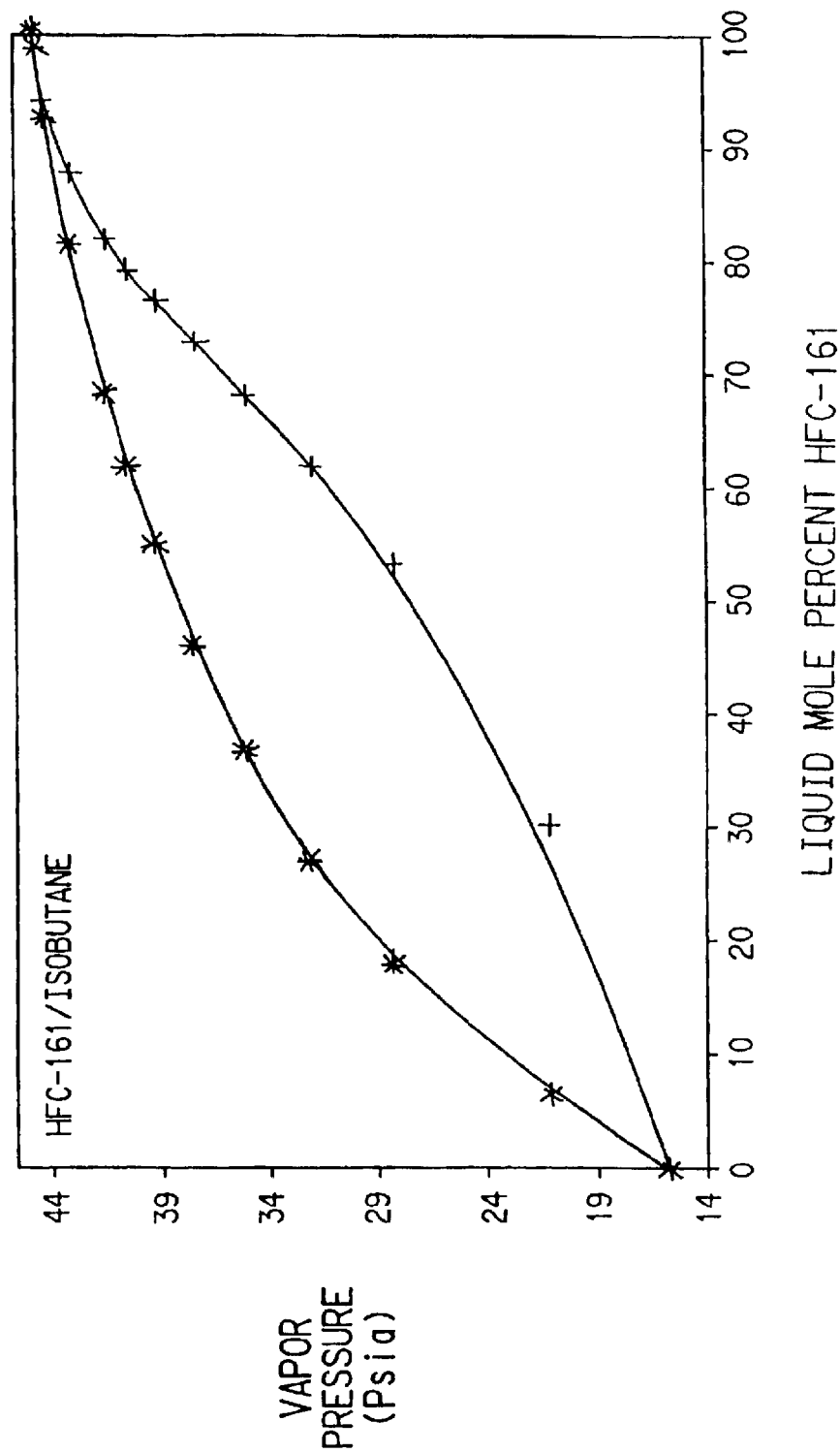
FIG. 6 is a graph of the vapor/liquid equilibrium curve for mixtures of HFC-161/isobutane at −10° C.
Figure 7:
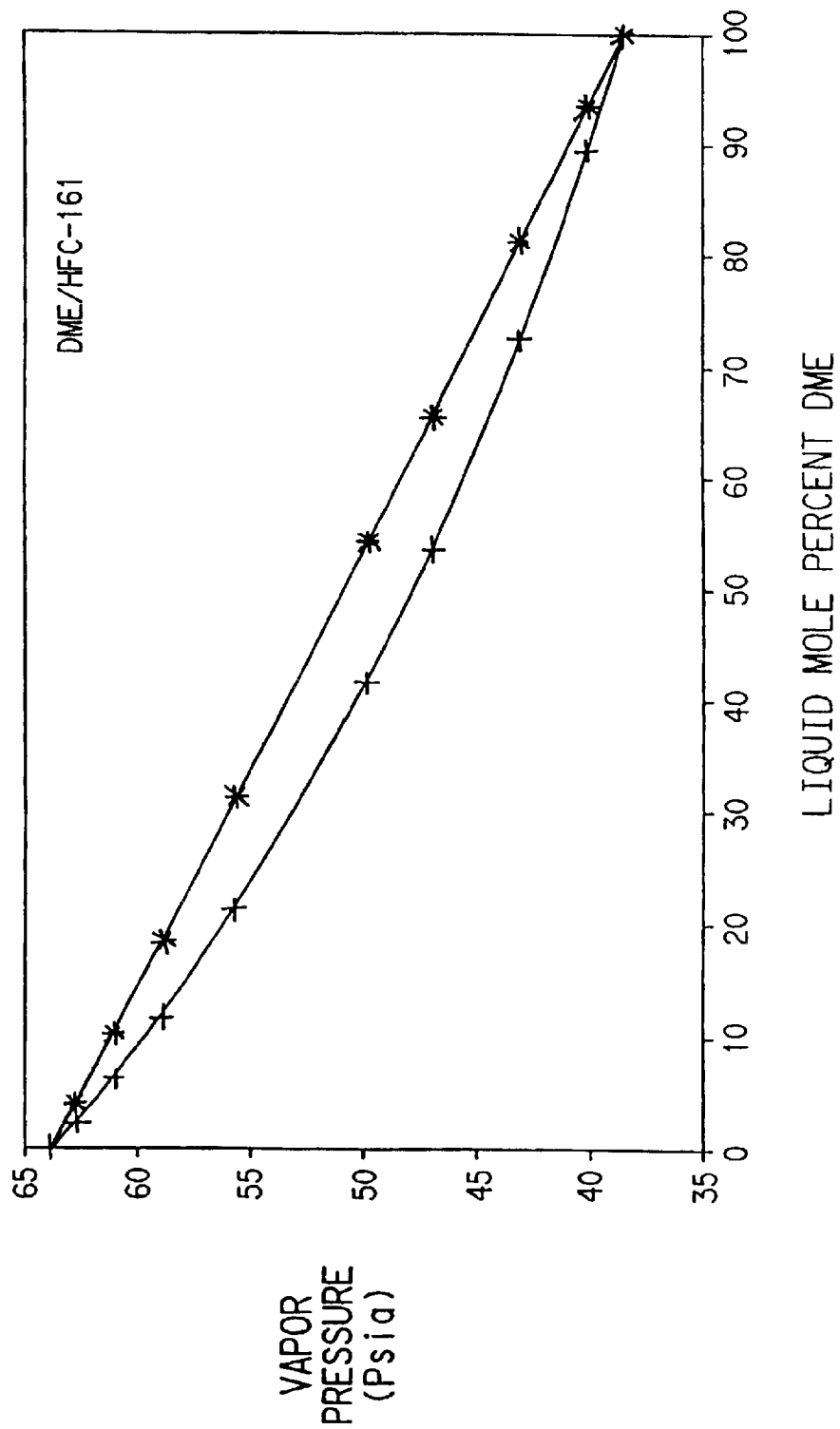
FIG. 7 is a graph of the vapor/liquid equilibrium curve for mixtures of HFC-161/DME at 0° C.
Figure 8:
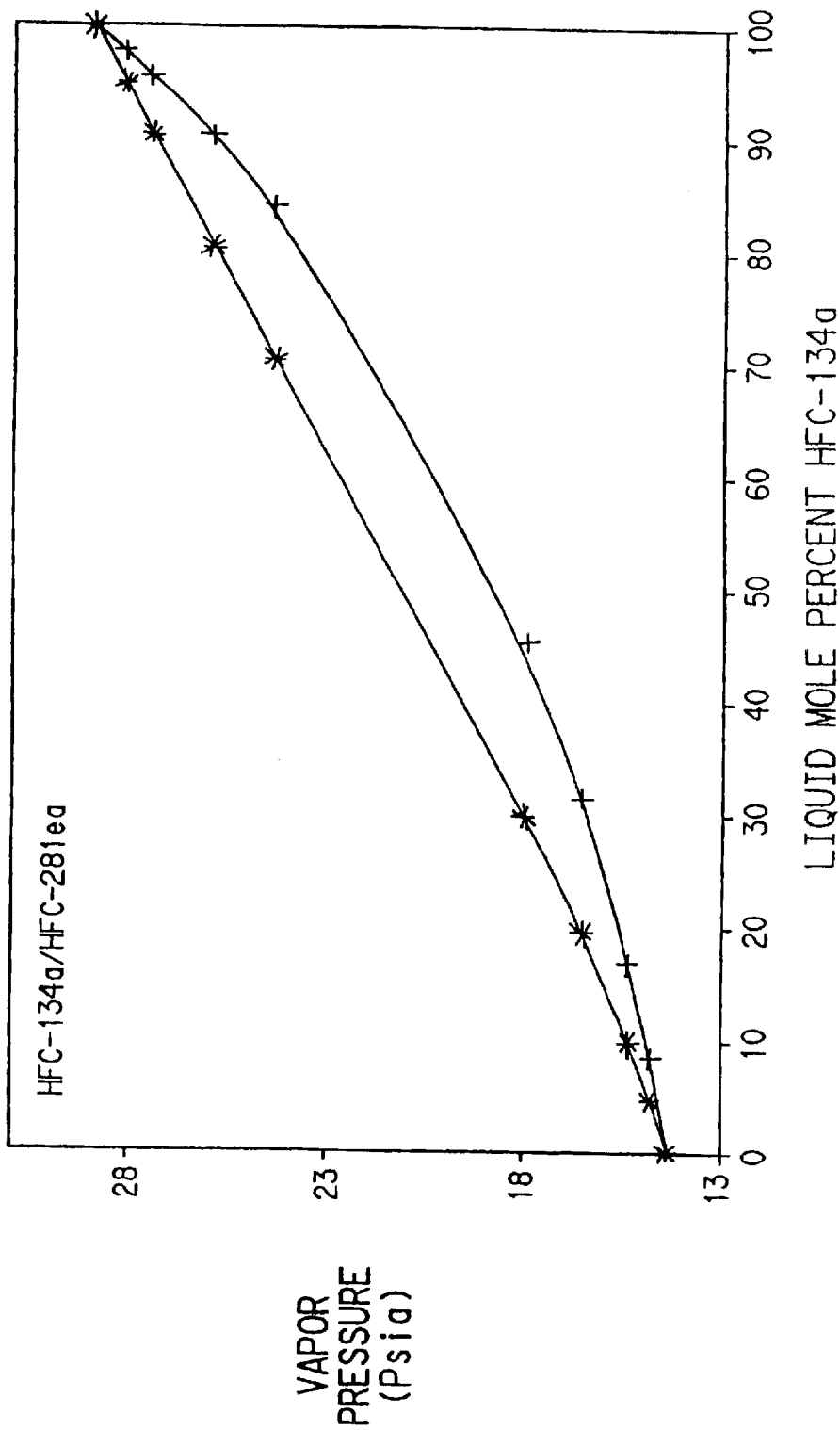
FIG. 8 is a graph of the vapor/liquid equilibrium curve for mixtures of HFC-281ea/HFC-134a at −10° C.
Figure 9:
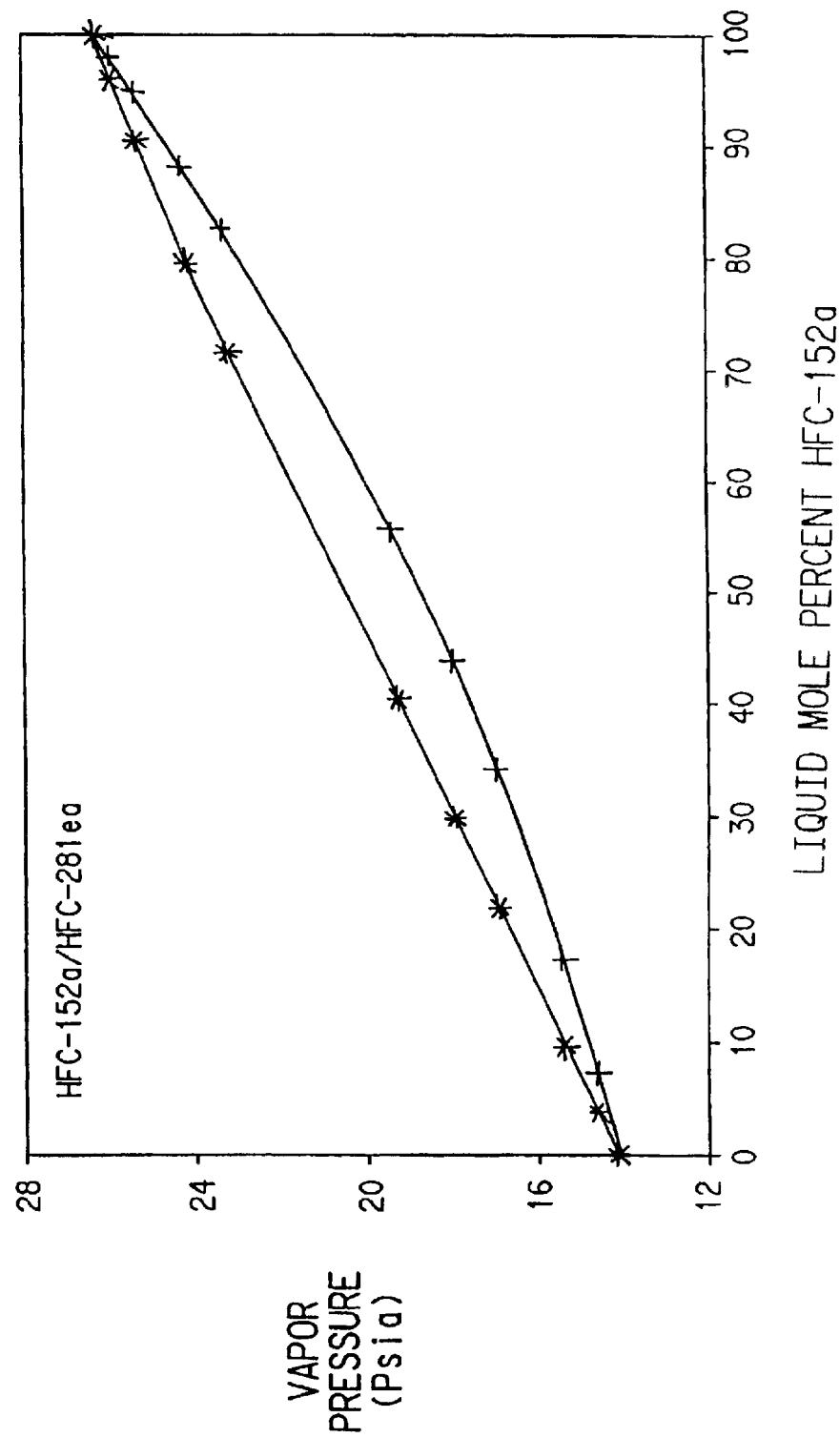
FIG. 9 is a graph of the vapor/liquid equilibrium curve for mixtures of HFC-281ea/HFC-152a at −10.01° C.
Figure 10:
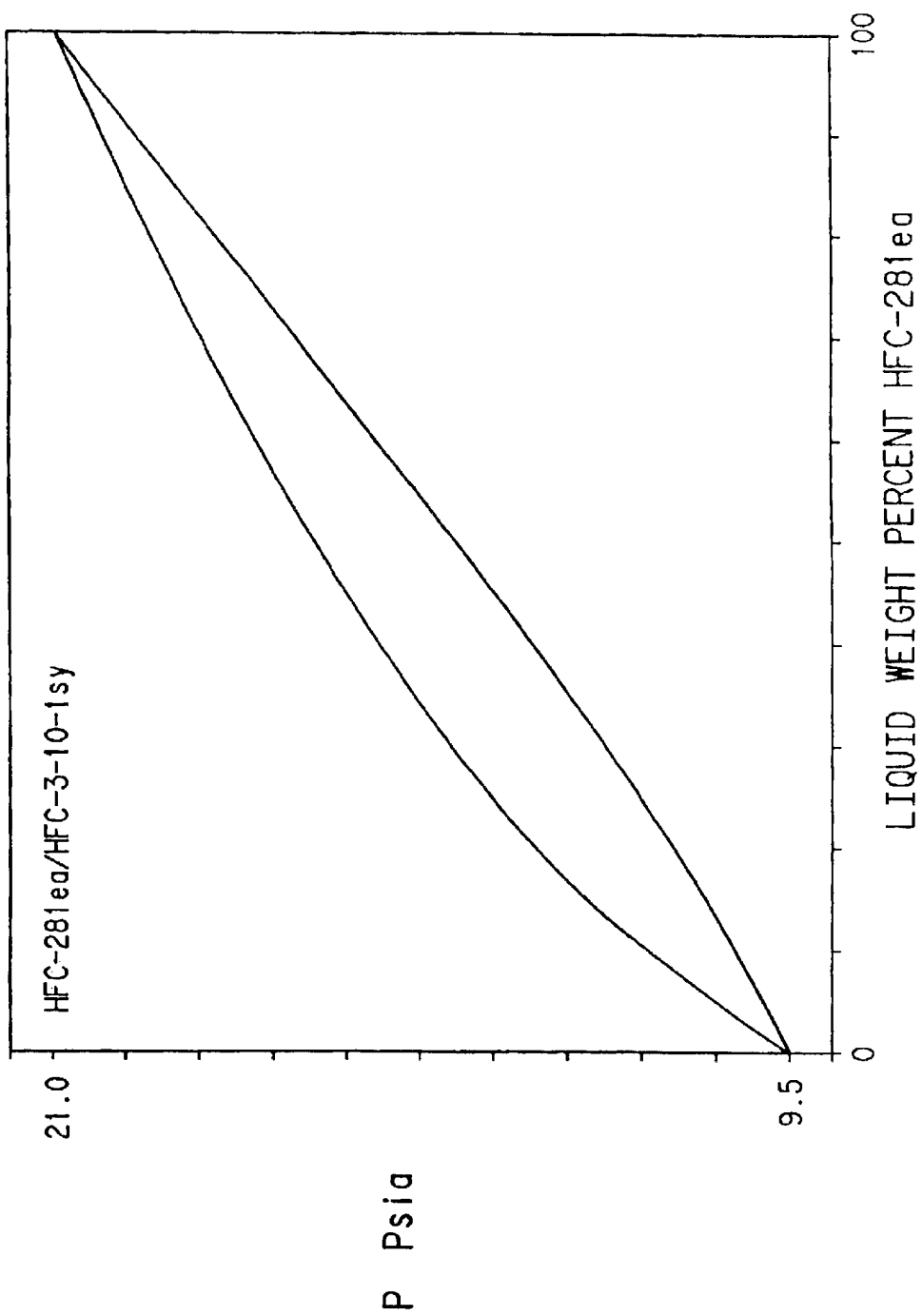
FIG. 10 is a graph of the vapor/liquid equilibrium curve for mixtures of HFC-281ea/HFC-3-10-1sy at 0° C.
Figure 11:
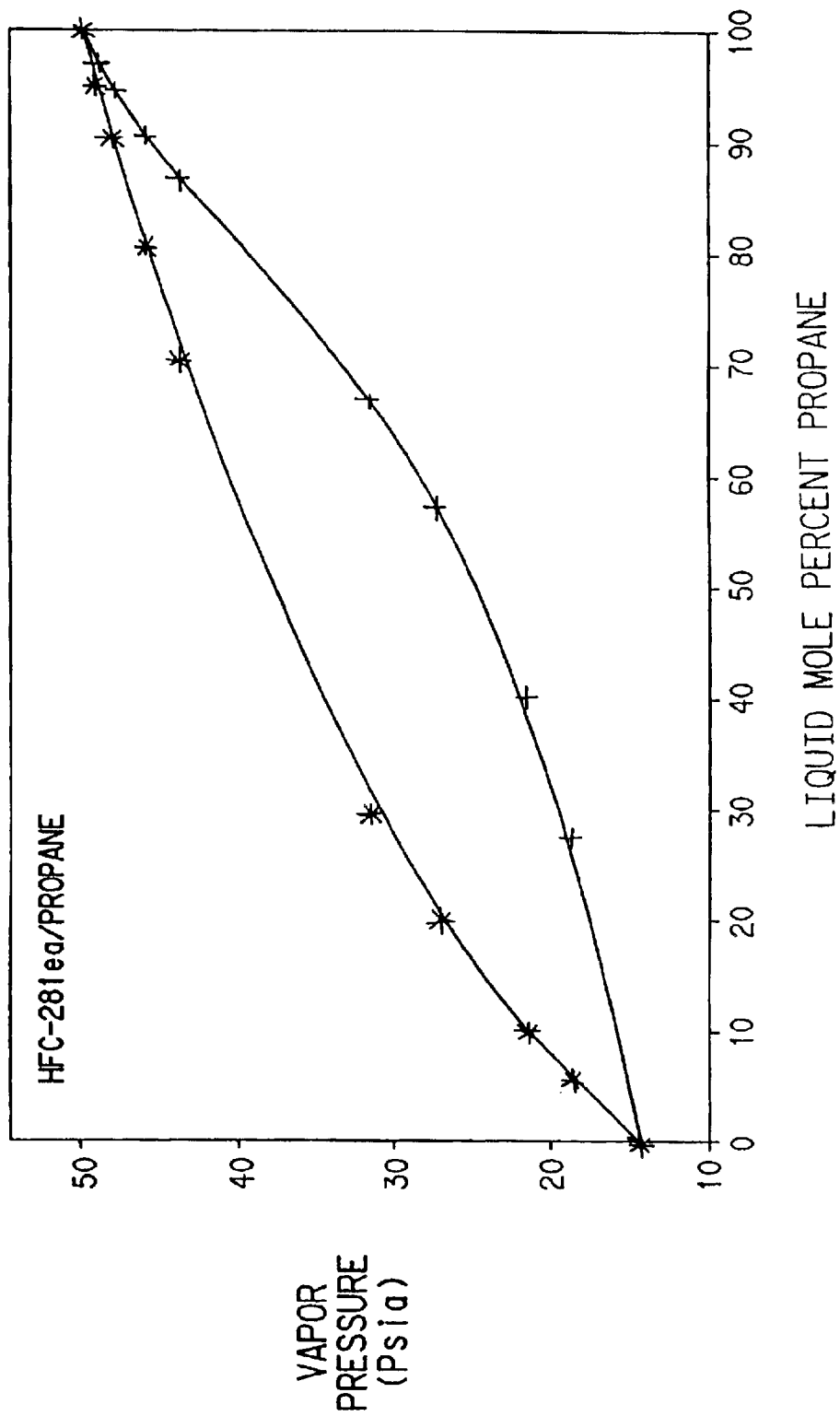
FIG. 11 is a graph of the vapor/liquid equilibrium curve for mixtures of HFC-281ea/propane at −10° C.
Figure 12:
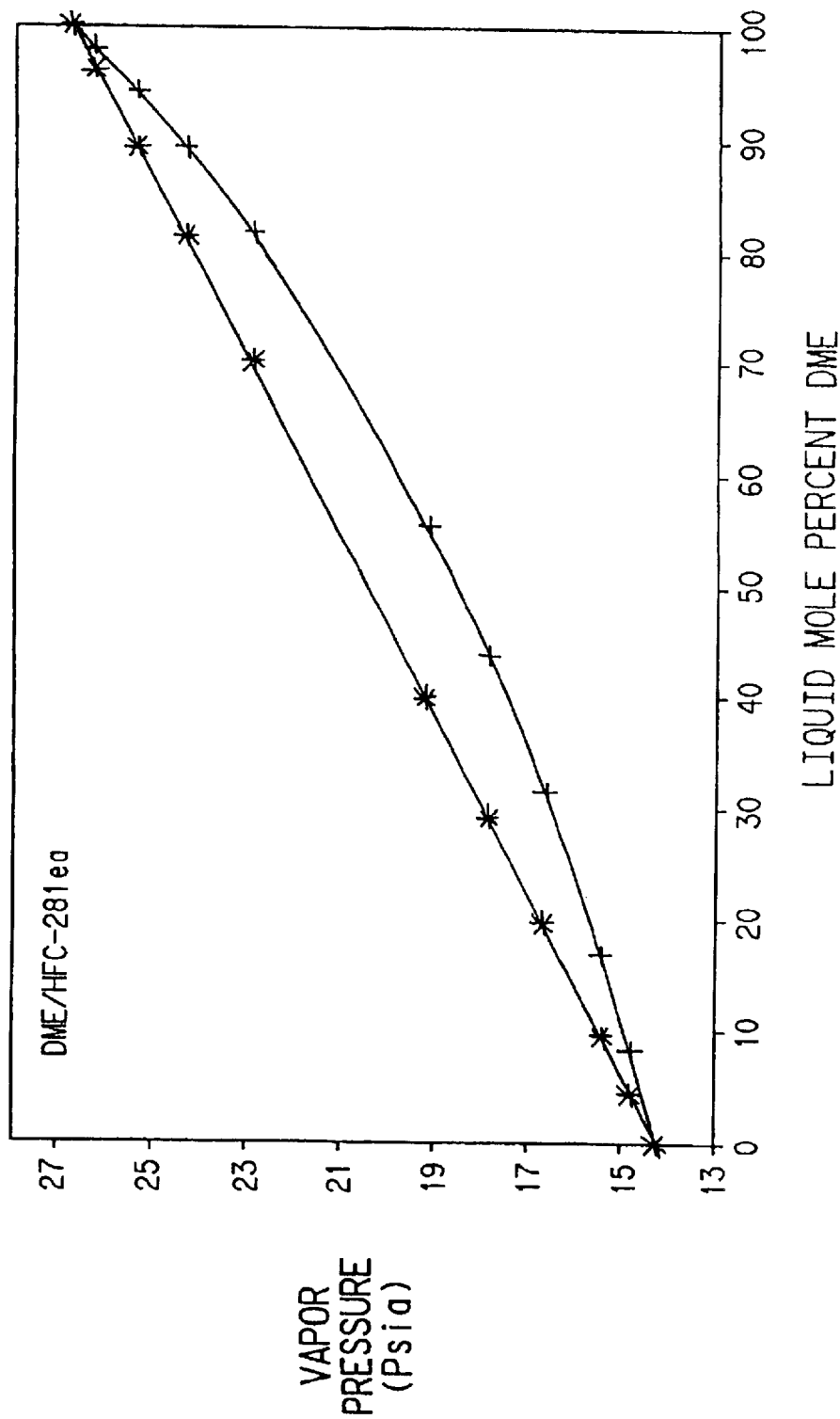
FIG. 12 is a graph of the vapor/liquid equilibrium curve for mixtures of HFC-281ea/DME at −9.95° C.
Figure 13:
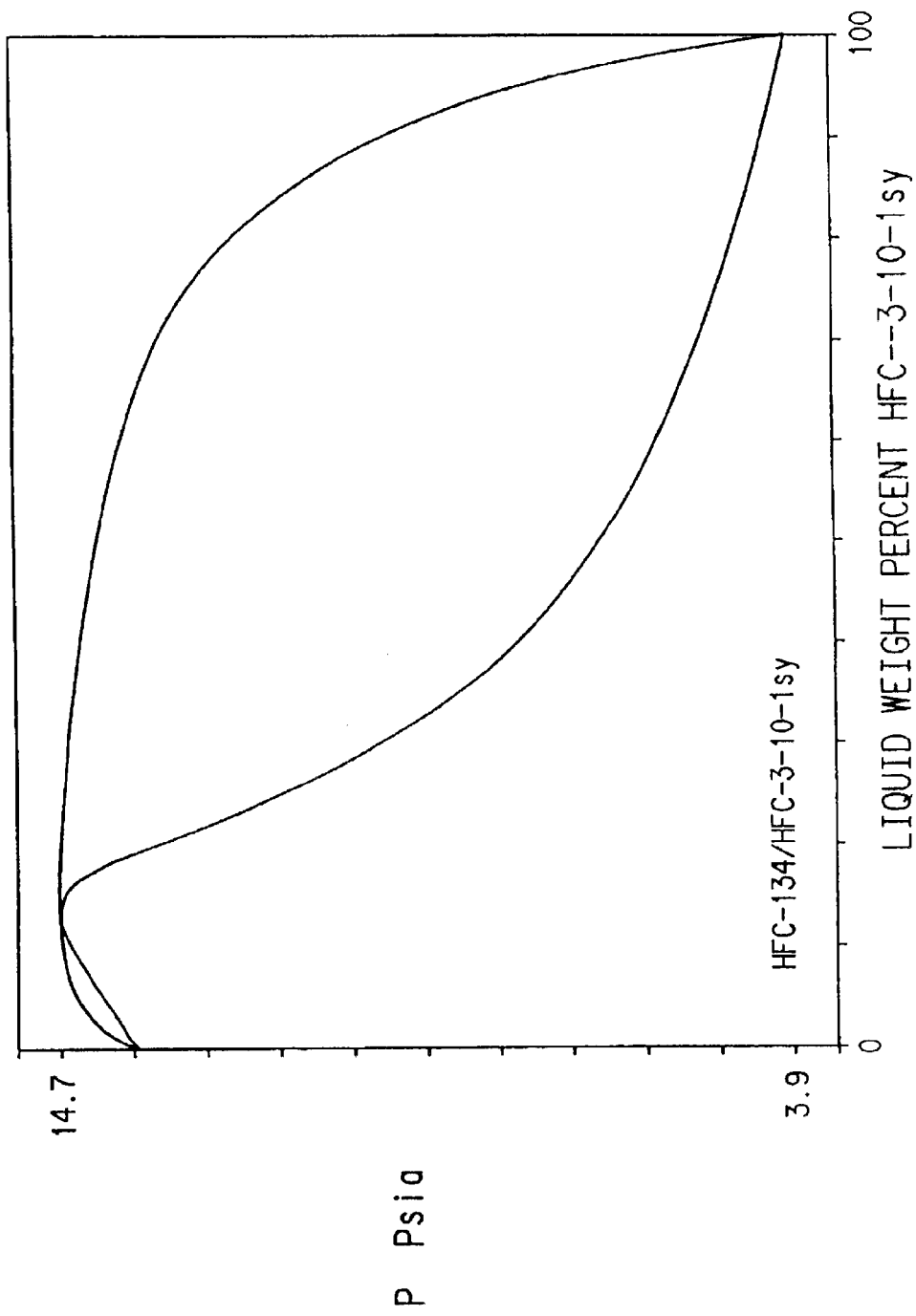
FIG. 13 is a graph of the vapor/liquid equilibrium curve for mixtures of HFC-3-10-1sy/HFC-134 at −21.7° C.
Figure 14:
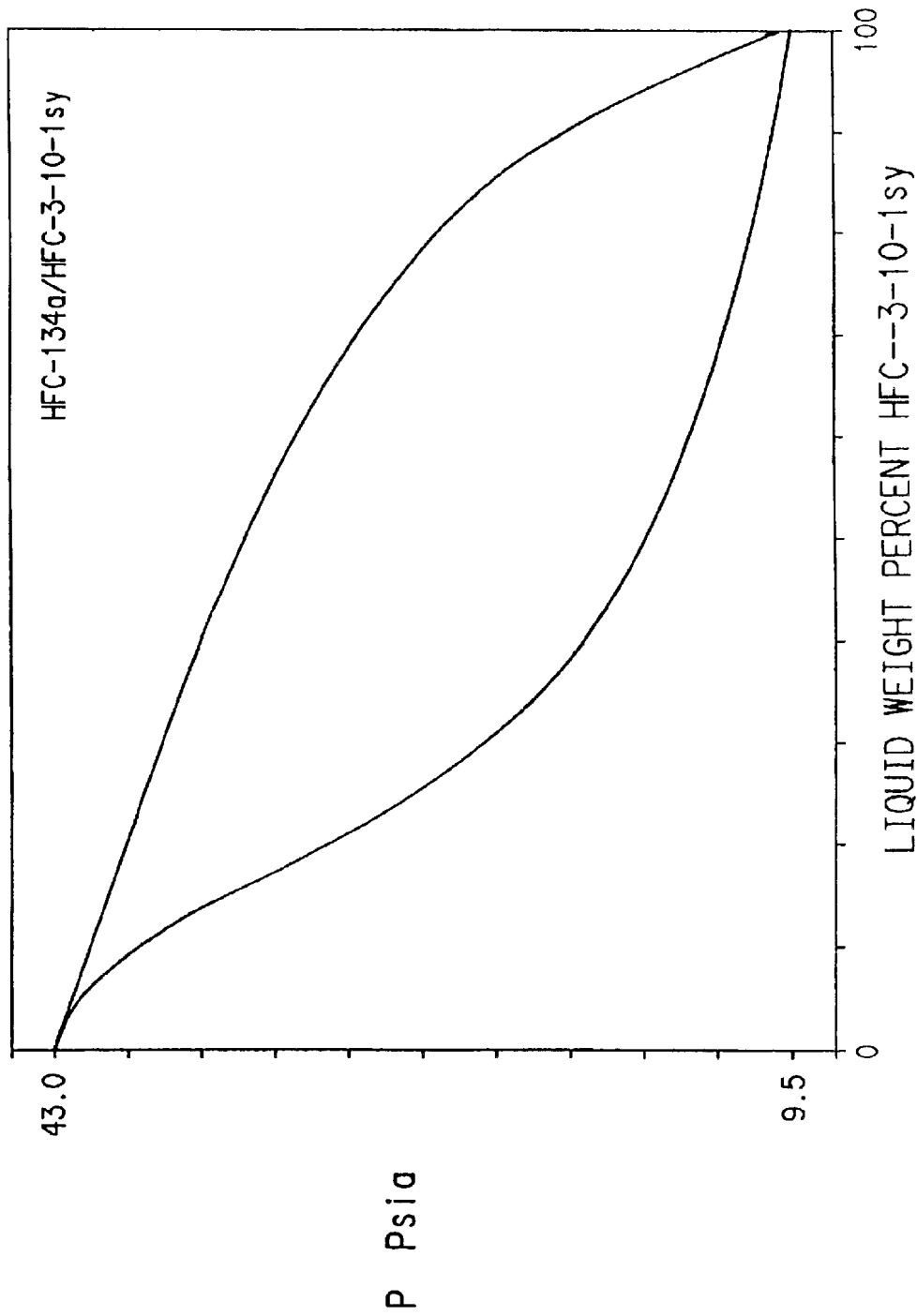
FIG. 14 is a graph of the vapor/liquid equilibrium curve for mixtures of HFC-3-10-1sy/HFC-134a at 0° C.
Figure 15:
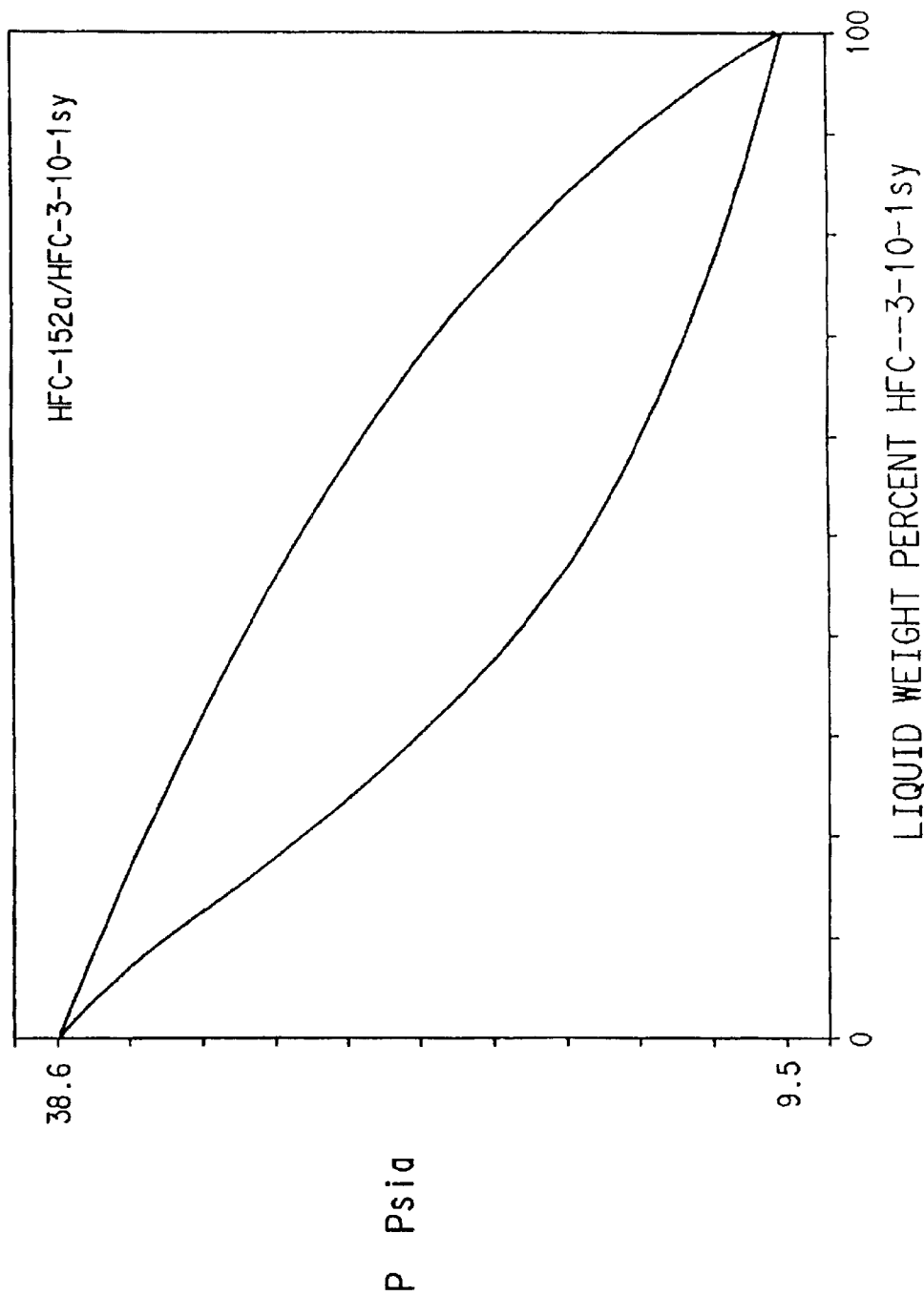
FIG. 15 is a graph of the vapor/liquid equilibrium curve for mixtures of HFC-3-10-1sy/HFC-152a at 0° C.
Figure 16:
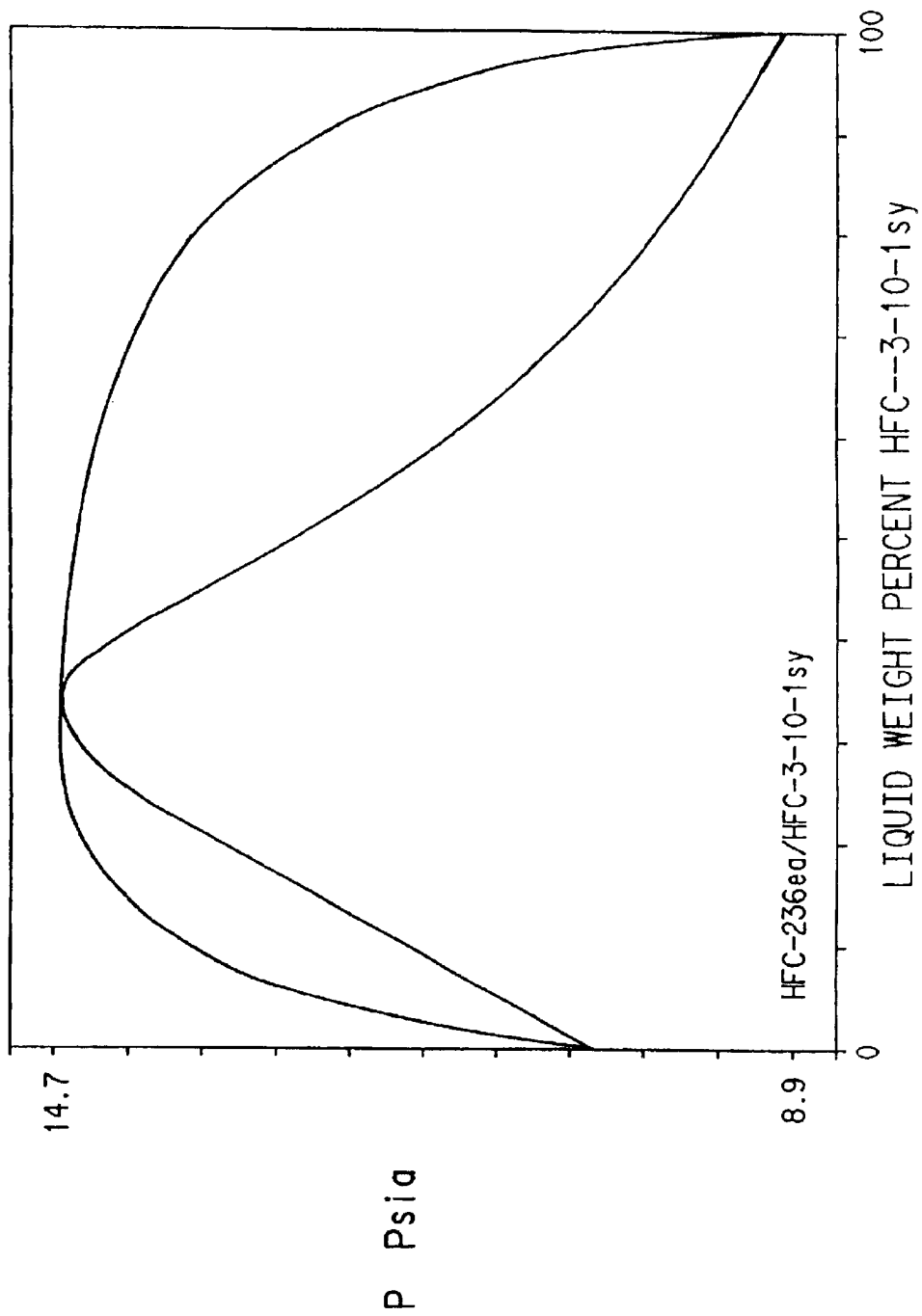
FIG. 16 is a graph of the vapor/liquid equilibrium curve for mixtures of HFC-3-10-1sy/HFC-236ea at −1.7° C.
Figure 17:
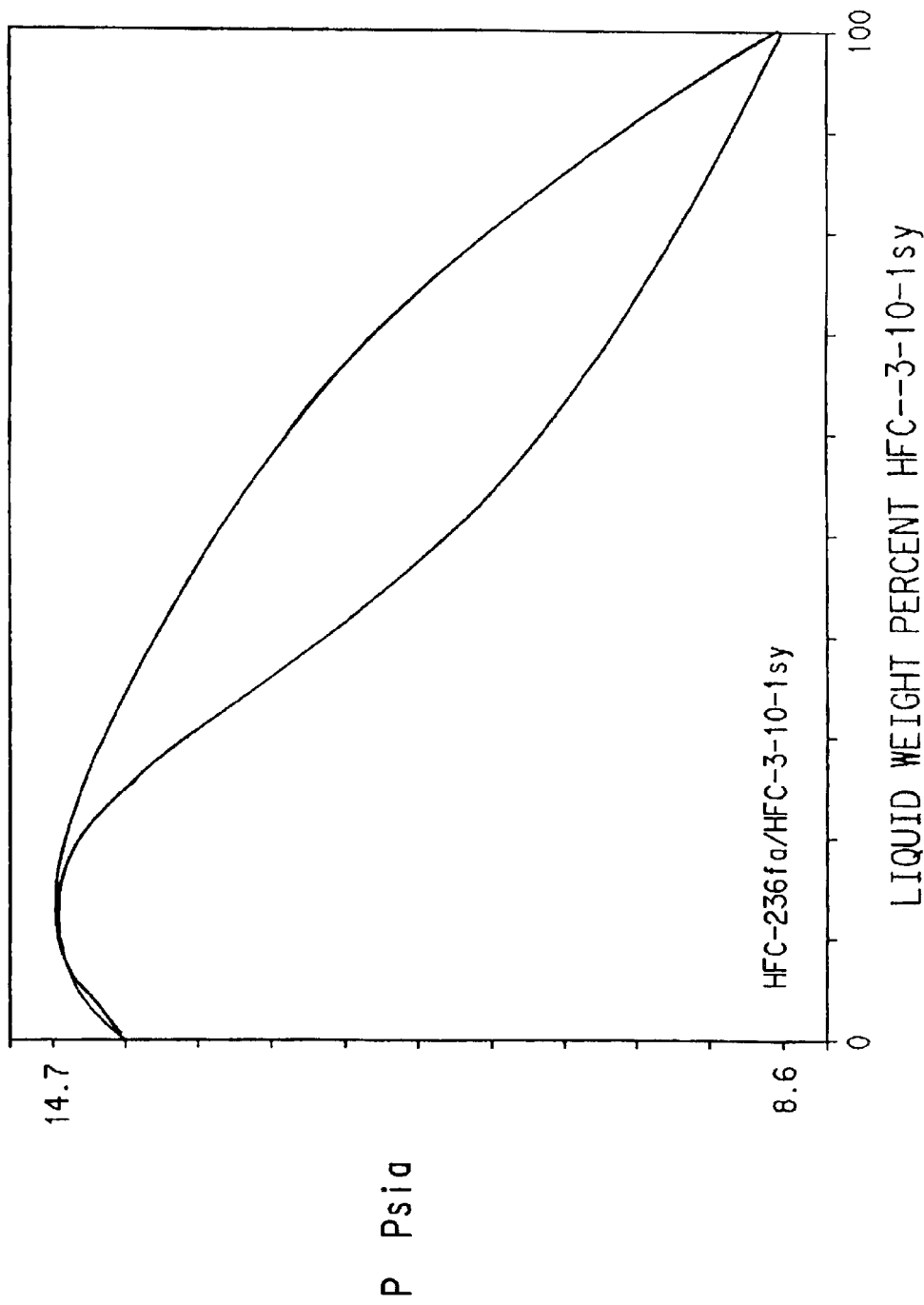
FIG. 17 is a graph of the vapor/liquid equilibrium curve for mixtures of HFC-3-10-1sy/HFC-236fa at −2.5° C.
Figure 18:
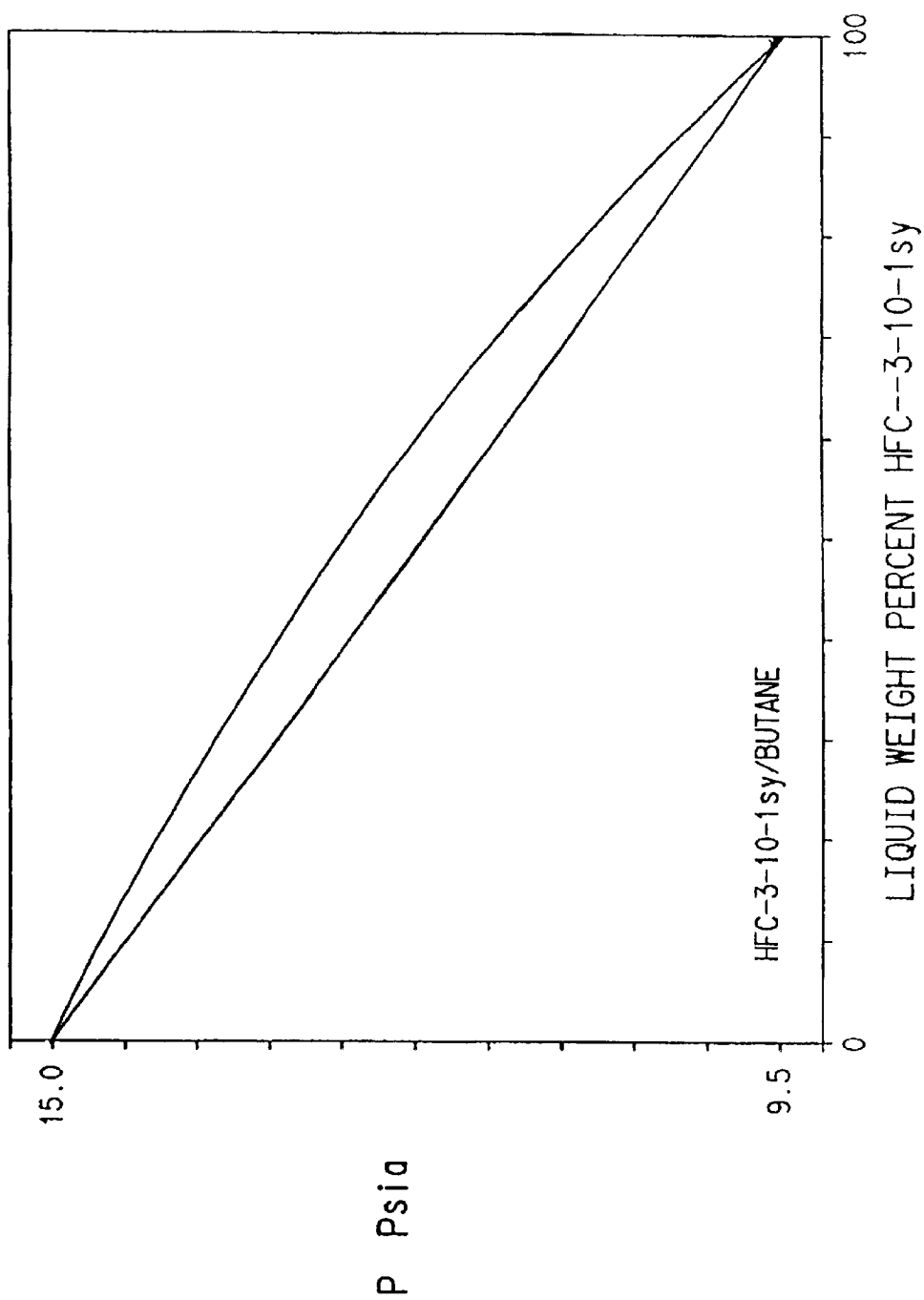
FIG. 18 is a graph of the vapor/liquid equilibrium curve for mixtures of HFC-3-10-1sy/butane at 0° C.
Figure 19:
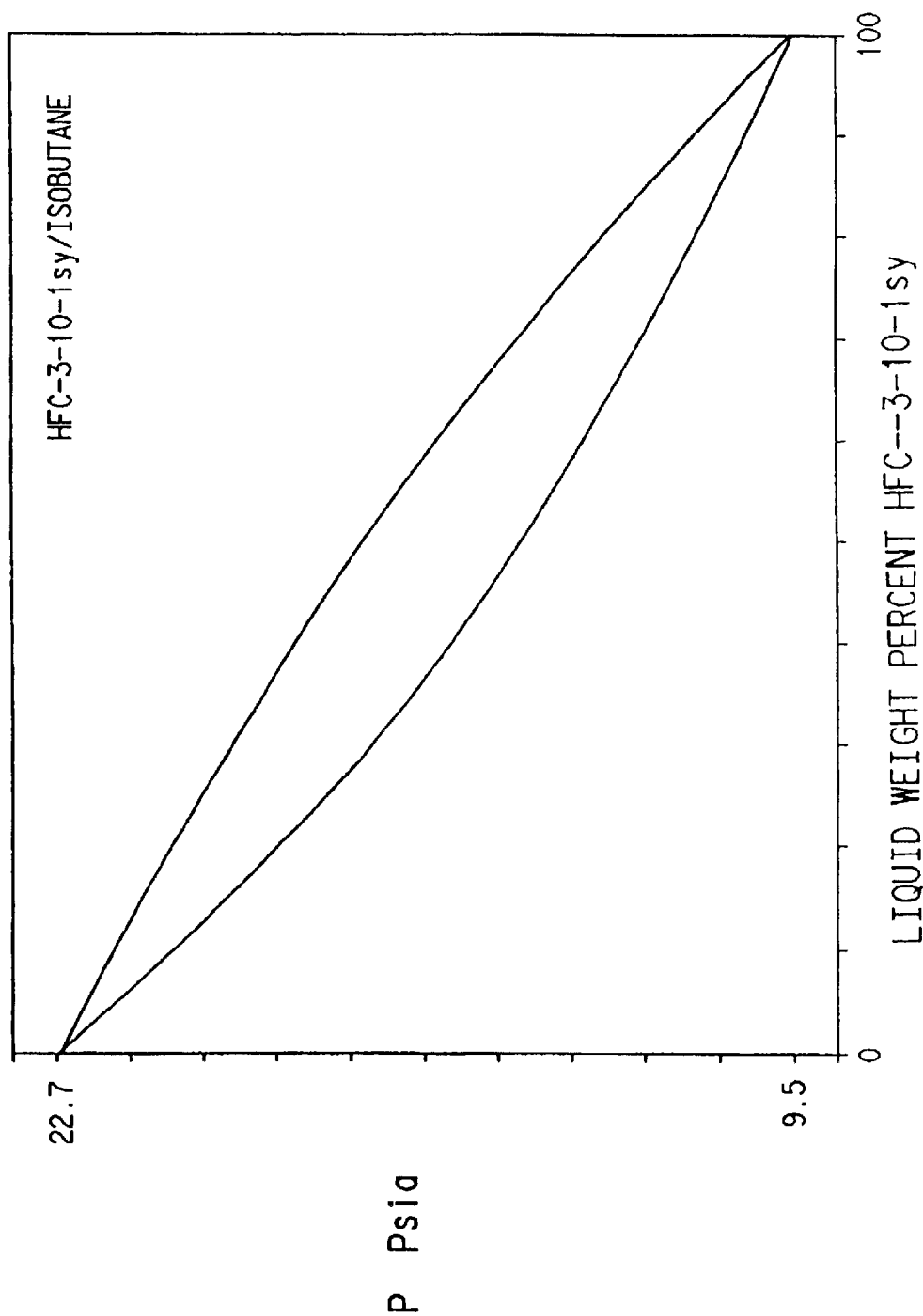
FIG. 19 is a graph of the vapor/liquid equilibrium curve for mixtures of HFC-3-10-1sy/isobutane at 0° C.
Figure 20:
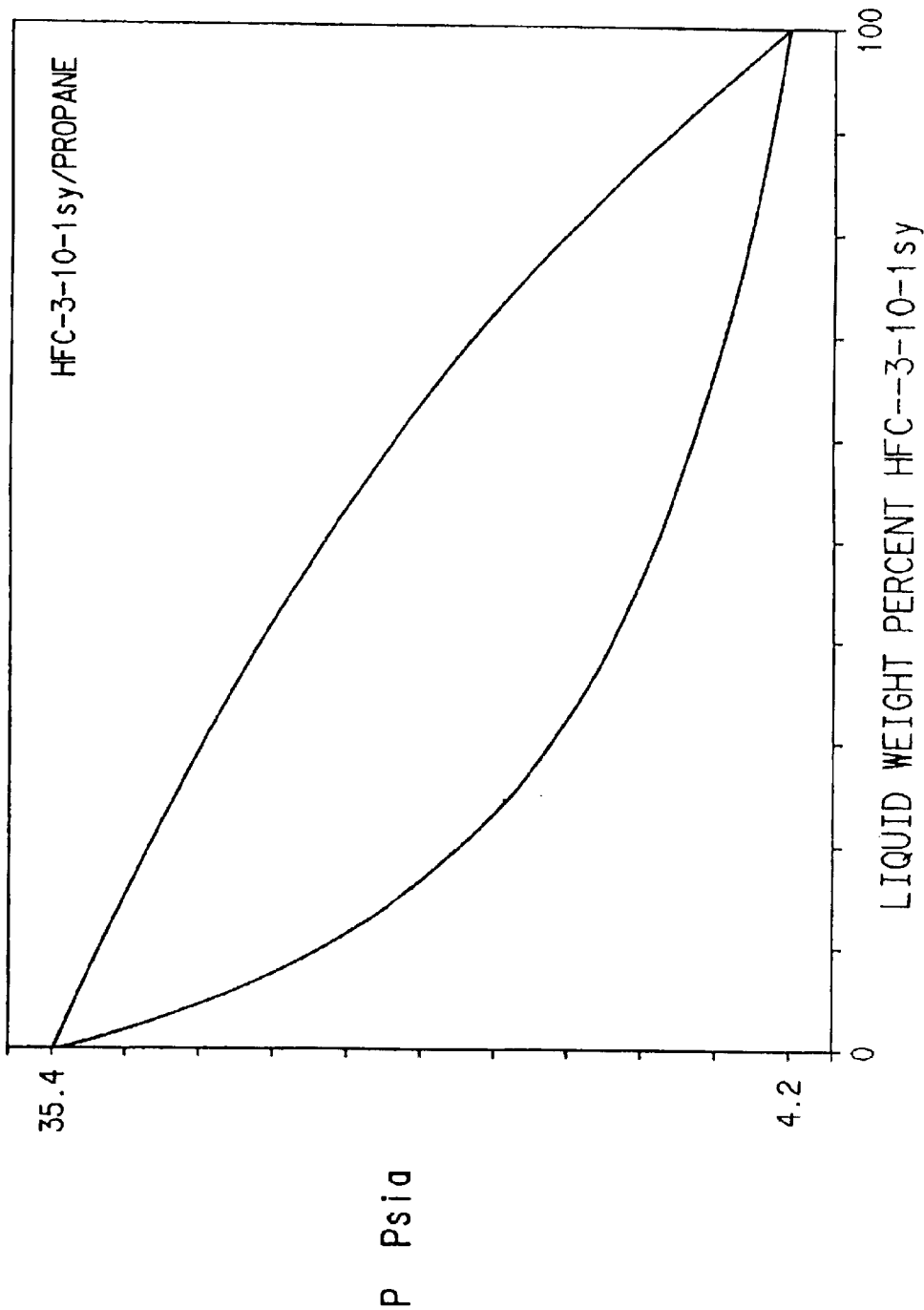
FIG. 20 is a graph of the vapor/liquid equilibrium curve for mixtures of HFC-3-10-1sy/propane at −20° C.
Figure 21:
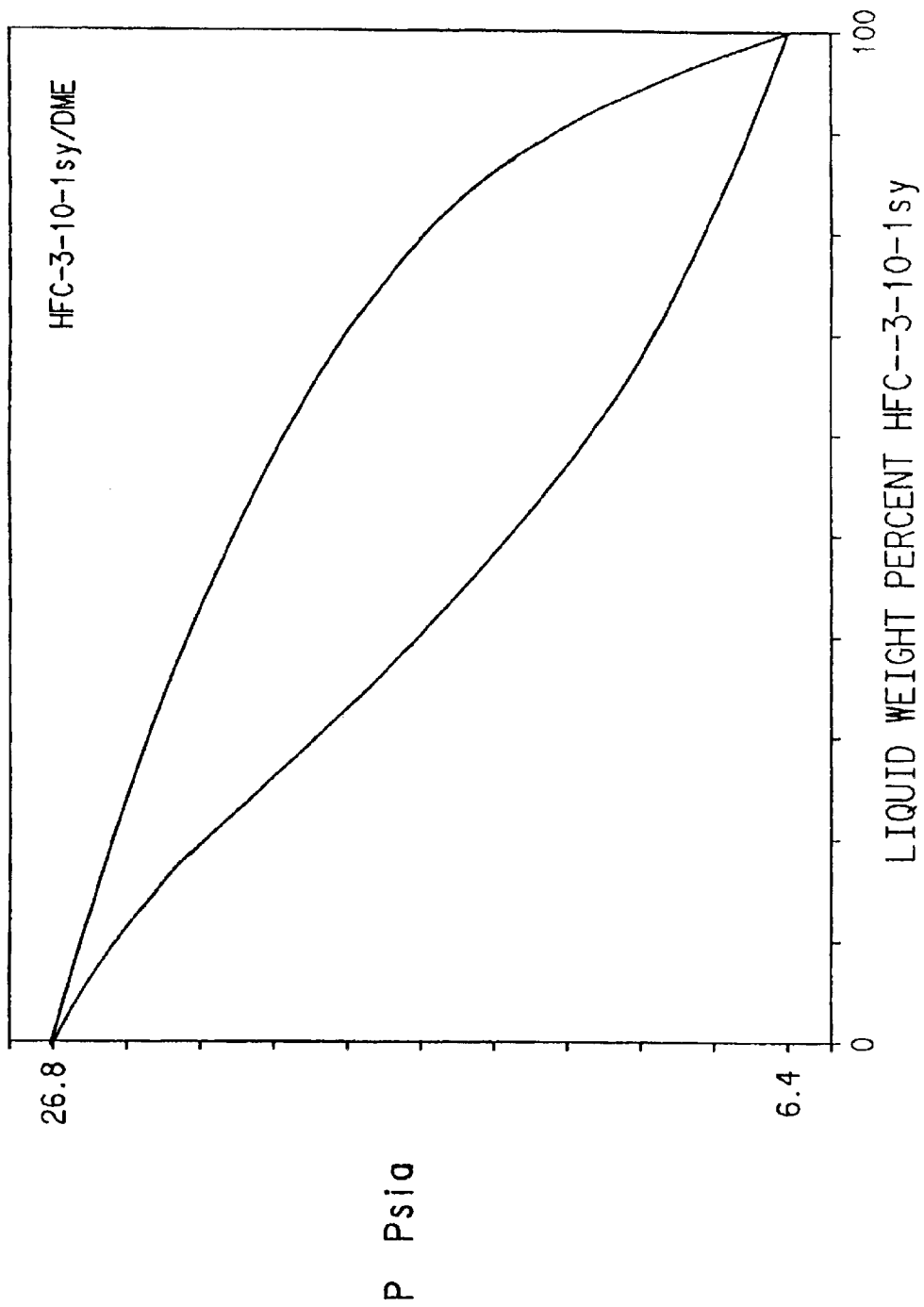
FIG. 21 is a graph of the vapor/liquid equilibrium curve for mixtures of HFC-3-10-1sy/DME at −10° C.

The present invention relates to the following compositions:

(a) fluoroethane (HFC-161);
(b) 2-fluoropropane (HFC-281ea);
(c) tert-butylfluoride (HFC-3-10-1sy);
(d) HFC-161 and 1,1,1,2-tetrafluoroethane (HFC-134a); HFC-161 and 1,1-difluoroethane (HFC-152a); HFC-161 and 2-fluoropropane (HFC-281ea); HFC-161 and tert-butylfluoride (HFC-3-10-1sy); HFC-161 and butane; HFC-161 and isobutane; or HFC-161 and dimethylether (DME);
(e) HFC-281ea and HFC-134a; HFC-281ea and HFC-152a; HFC-281ea and HFC-3-10-1sy; HFC-281ea and propane; or HFC-281ea and DME; or
(f) HFC-3-10-1sy and 1,1,2,2-tetrafluoroethane (HFC-134); HFC-3-10-1sy and HFC-134a; HFC-3-10-1sy and HFC-152a; HFC-3-10-1sy and 1,1,1,2,3,3-hexafluoropropane (HFC-236ea); HFC-3-10-1sy and 1,1,1,3,3,3-hexafluoropropane (HFC-236fa); HFC-3-10-1sy and butane; HFC-3-10-1sy and isobutane; HFC-3-10-1sy and propane; or HFC-3-10-1sy and DME.

1–99 wt. % of each of the components of the compositions are useful as aerosol propellants, refrigerants, cleaning agents, expansion agents for polyolefins and polyurethanes, refrigerants, heat transfer media, gaseous dielectrics, fire extinguishing agents, power cycle working fluids, polymerization media, particulate removal fluids, carrier fluids, buffing abrasive agents, and displacement drying agents. Further, the present invention also relates to the discovery of azeotropic or azeotrope-like compositions of effective amounts of each of the above mixtures to form an azeotropic or azeotrope-like composition.

By "azeotropic" composition is meant a constant boiling liquid admixture of two or more substances that behaves as a single substance. One way to characterize an azeotropic composition is that the vapor produced by partial evaporation or distillation of the liquid has the same composition as the liquid from which it was evaporated or distilled, that is, the admixture distills/refluxes without compositional change. Constant boiling compositions are characterized as azeotropic because they exhibit either a maximum or minimum boiling point, as compared with that of the non-azeotropic mixtures of the same components.

By "azeotrope-like" composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, that is, the admixture distills/refluxes without substantial composition change. Another way to characterize an azeotrope-like composition is that the bubble point vapor pressure and the dew point vapor pressure of the composition at a particular temperature are substantially the same.

It is recognized in the art that a composition is azeotrope-like if, after 50 weight percent of the composition is removed such as by evaporation or boiling off, the difference in vapor pressure between the original composition and the composition remaining after 50 weight percent of the original composition has been removed is less than about 10 percent, when measured in absolute units. By absolute units, it is meant measurements of pressure and, for example, psia, atmospheres, bars, torr, dynes per square centimeter, millimeters of mercury, inches of water and other equivalent terms well known in the art. If an azeotrope is present, there is no difference in vapor pressure between the original composition and the composition remaining after 50 weight percent of the original composition has been removed.

Therefore, included in this invention are compositions of effective amounts of:

(a) HFC-161 and 1,1,1,2-tetrafluoroethane (HFC-134a); HFC-161 and 1,1-difluoroethane (HFC-152a); HFC-161 and 2-fluoropropane (HFC-281ea); HFC-161 and tert-butylfluoride (HFC-3-10-1sy); HFC-161 and butane; HFC-161 and isobutane; or HFC-161 and dimethylether (DME);

(b) HFC-281ea and HFC-134a; HFC-281ea and HFC-152a; HFC-281ea and HFC-3-10-1sy; HFC-281ea and propane; or HFC-281ea and DME; or (c) HFC-3-10-1sy and 1,1,2,2-tetrafluoroethane (HFC-134); HFC-3-10-1sy and HFC-134a; HFC-3-10-1sy and HFC-152a; HFC-3-10-1sy and 1,1,1,2,3,3-hexafluoropropane (HFC-236ea); HFC-3-10-1sy and 1,1,1,3,3,3-hexafluoropropane (HFC-236fa); HFC-3-10-1sy and butane; HFC-3-10-1sy and isobutane; HFC-3-10-1sy and propane; or HFC-3-10-1sy and DME;

such that after 50 weight percent of an original composition is evaporated or boiled off to produce a remaining composition, the difference in the vapor pressure between the original composition and the remaining composition is 10 percent or less.

For compositions that are azeotropic, there is usually some range of compositions around the azeotrope point that, for a maximum boiling azeotrope, have boiling points at a particular pressure higher than the pure components of the composition at that pressure and have vapor pressures at a particular temperature lower than the pure components of the composition at that temperature, and that, for a minimum boiling azeotrope, have boiling points at a particular pressure lower than the pure components of the composition at that pressure and have vapor pressures at a particular temperature higher than the pure components of the composition at that temperature. Boiling temperatures and vapor pressures above or below that of the pure components are caused by unexpected intermolecular forces between and among the molecules of the compositions, which can be a combination of repulsive and attractive forces such as van der Waals forces and hydrogen bonding.

The range of compositions that have a maximum or minimum boiling point at a particular pressure, or a maximum or minimum vapor pressure at a particular temperature, may or may not be coextensive with the range of compositions that have a change in vapor pressure of less than about 10% when 50 weight percent of the composition is evaporated. In those cases where the range of compositions that have maximum or minimum boiling temperatures at a particular pressure, or maximum or minimum vapor pressures at a particular temperature, are broader than the range of compositions that have a change in vapor pressure of less than about 10% when 50 weight percent of the composition is evaporated, the unexpected intermolecular forces are nonetheless believed important in that the refrigerant compositions having those forces that are not substantially constant boiling may exhibit unexpected increases in the capacity or efficiency versus the components of the refrigerant composition.

Substantially constant boiling, azeotropic or azeotrope-like compositions of this invention comprise the following:

| COMPONENTS | T° C. | WEIGHT RANGES (wt. %/wt./ %) | PREFERRED (wt. %/wt. %) |
|---|---|---|---|
| HFC-161/HFC-134a | −20 | 1–99/1–99 | 10–90/10–90 |
| HFC-161/HFC-152a | −30 | 1–99/1–99 | 10–90/10–90 |
| HFC-161/HFC-281ea | −10 | 73–99/1–27 | 73–99/1–27 |
| HFC-161/HFC-3-10-1sy | −20 | 75–99/1–25 | 75–99/1–25 |
| HFC-161/butane | −20 | 67–99/1–33 | 67–99/1–33 |
| HFC-161/isobutane | −20 | 52–99/1–48 | 52–99/1–48 |
| HFC-161/DME | −30 | 1–99/1–99 | 10–90/10–90 |
| HFC-281ea/HFC-134a | −10 | 1–99/1–99 | 10–90/10/90 |
| HFC-281ea/HFC-152a | −20 | 1–99/1–99 | 10–90/10–90 |
| HFC-281ea/HFC-3-10-1sy | 0 | 41–99/1–59 | 41–99/1–59 |
| HFC-281ea/propane | −10 | 1–41/59–99 | 1–41/59–99 |
| HFC-281ea/DME | −9.95 | 1–99/1–99 | 10–90/10–90 |
| HFC-3-10-1sy/HFC-134 | −21.7 | 1–44/56–99 | 1–44/56–99 |
| HFC-3-10-1sy/HFC-134a | 0 | 1–32/68–99 | 1–32/68–99 |
| HFC-3-10-1sy/HFC-152a | 0 | 1–30/70–99 | 1–30/70–99 |
| HFC-3-10-1sy/HFC-236ea | −1.7 | 11–60/40–89 and 1–3/97–99 | 11–60/40–89 and 1–3/97–99 |
| HFC-3-10-1sy/HFC-236fa | −2.5 | 1–52/48–99 | 1–52/48–99 |
| HFC-3-10-1sy/butane | 0 | 1–99/1–99 | 10–90/10–90 |
| HFC-3-10-1sy/isobutane | 0 | 1–45/55–99 and 89–99/1–11 | 1–45/55–99 and 89–99/1–11 |
| HFC-3-10-1sy/propane | −20 | 1–19/81–99 | 1–19/81–99 |
| HFC-3-10-1sy/DME | −10 | 1–42/58–99 | 1–42/58–99 |

For purposes of this invention, "effective amount" is defined as the amount of each component of the inventive compositions which, when combined, results in the formation of an azeotropic or azeotrope-like composition. This definition includes the amounts of each component, which amounts may vary depending on the pressure applied to the composition so long as the azeotropic or azeotrope-like compositions continue to exist at the different pressures, but with possible different boiling points.

Therefore, effective amount includes the amounts, such as may be expressed in weight percentages, of each component of the compositions of the instant invention which form azeotropic or azeotrope-like compositions at temperatures or pressures other than as described herein.

For the purposes of this discussion, azeotropic or constant-boiling is intended to mean also essentially azeotropic or essentially-constant boiling. In other words, included within the meaning of these terms are not only the true azeotropes described above, but also other compositions containing the same components in different proportions, which are true azeotropes at other temperatures and pressures, as well as those equivalent compositions which are part of the same azeotropic system and are azeotrope-like in their properties. As is well recognized in this art, there is a range of compositions which contain the same components as the azeotrope, which will not only exhibit essentially equivalent properties for refrigeration and other applications, but which will also exhibit essentially equivalent properties to the true azeotropic composition in terms of constant boiling characteristics or tendency not to segregate or fractionate on boiling.

It is possible to characterize, in effect, a constant boiling admixture which may appear under many guises, depending upon the conditions chosen, by any of several criteria:

The composition can be defined as an azeotrope of A, B, C (and D . . . ) since the very term "azeotrope" is at once both definitive and limitative, and requires that effective amounts of A, B, C (and D . . . ) for this unique composition of matter which is a constant boiling composition.

It is well known by those skilled in the art, that, at different pressures, the composition of a given azeotrope will vary at least to some degree, and changes in pressure will also change, at least to some degree, the boiling point temperature. Thus, an azeotrope of A, B, C (and D . . . ) represents a unique type of relationship but with a variable composition which depends on temperature and/or pressure. Therefore, compositional ranges, rather than fixed compositions, are often used to define azeotropes.

The composition can be defined as a particular weight percent relationship or mole percent relationship of A, B, C (and D . . . ), while recognizing that such specific values point out only one particular relationship and that in actuality, a series of such relationships, represented by A, B, C (and D . . . ) actually exist for a given azeotrope, varied by the influence of pressure.

An azeotrope of A, B, C (and D . . . ) can be characterized by defining the compositions as an azeotrope characterized by a boiling point at a given pressure, thus giving identifying characteristics without unduly limiting the scope of the invention by a specific numerical composition, which is limited by and is only as accurate as the analytical equipment available.

The azeotrope or azeotrope-like compositions of the present invention can be prepared by any convenient method including mixing or combining the desired amounts. A preferred method is to weigh the desired component amounts and thereafter combine them in an appropriate container.

Specific examples illustrating the invention are given below. Unless otherwise stated therein, all percentages are by weight. It is to be understood that these examples are merely illustrative and in no way are to be interpreted as limiting the scope of the invention.

EXAMPLE 1

Phase Study

A phase study shows the following compositions are azeotropic, all at the temperature specified.

| Components | T ° C. | Weight Ranges | Vapor Press. psia | (kPa) |
|---|---|---|---|---|
| HFC-3-10-1sy/HFC-134 | −21.7 | 13.9/86.1 | 14.7 | 101 |
| HFC-3-10-1sy/HFC-236ea | −1.7 | 33.6/66.4 | 14.7 | 101 |
| HFC-3-10-1sy/HFC-236fa | −2.5 | 12.7/87.3 | 14.7 | 101 |

EXAMPLE 2

Impact of Vapor Leakage

A vessel is charged with an initial composition at a specified temperature, and the initial vapor pressure of the composition is measured. The composition is allowed to leak from the vessel, while the temperature is held constant, until 50 weight percent of the initial composition is removed, at which time the vapor pressure of the composition remaining in the vessel is measured. The results are summarized below.

| | INITIAL | | 50% LEAK | | |
|---|---|---|---|---|---|
| WT % A/WT % B | PSIA | KPA | PSIA | KPA | DELTA % P |
| HFC-161/HFC-134a (−20° C.) | | | | | |
| 1/99 | 19.6 | 135 | 19.5 | 134 | 0.5 |
| 10/90 | 22.0 | 152 | 21.2 | 146 | 3.6 |
| 20/80 | 24.1 | 166 | 22.9 | 158 | 5.0 |
| 30/70 | 25.8 | 178 | 24.6 | 170 | 4.7 |
| 40/60 | 27.2 | 188 | 26.1 | 180 | 4.0 |
| 50/50 | 28.3 | 195 | 27.5 | 190 | 2.8 |
| 60/40 | 29.2 | 201 | 28.6 | 197 | 2.1 |
| 70/30 | 29.9 | 206 | 29.5 | 203 | 1.3 |
| 80/20 | 30.5 | 210 | 30.3 | 209 | 0.7 |
| 90/10 | 30.9 | 213 | 30.8 | 212 | 0.3 |
| 99/1 | 31.2 | 215 | 31.2 | 215 | 0.0 |
| HFC-161/HFC-152a (−30° C.) | | | | | |
| 1/99 | 11.7 | 80.7 | 11.7 | 80.7 | 0.0 |
| 10/90 | 12.7 | 87.6 | 12.3 | 84.8 | 3.1 |
| 20/80 | 13.8 | 95.1 | 13.1 | 90.3 | 5.1 |
| 30/70 | 14.9 | 103 | 14.0 | 96.5 | 6.0 |
| 40/60 | 15.9 | 110 | 14.9 | 103 | 6.3 |
| 50/50 | 16.9 | 117 | 15.9 | 110 | 5.9 |
| 60/40 | 17.8 | 123 | 16.9 | 117 | 5.1 |
| 70/30 | 18.7 | 129 | 18.0 | 124 | 3.7 |
| 80/20 | 19.5 | 134 | 19.0 | 131 | 2.6 |
| 90/10 | 20.3 | 140 | 20.0 | 138 | 1.5 |
| 99/1 | 20.9 | 144 | 20.9 | 144 | 0.0 |
| HFC-161/HFC-281ea (−10° C.) | | | | | |
| 99/1 | 44.9 | 310 | 44.8 | 309 | 0.2 |
| 90/10 | 42.7 | 294 | 41.1 | 283 | 3.7 |
| 80/20 | 40.0 | 276 | 37.1 | 256 | 7.2 |
| 73/27 | 38.1 | 263 | 34.3 | 236 | 10.0 |
| HFC-161/HFC-3-10-1sy (−20° C.) | | | | | |
| 99/1 | 31.1 | 214 | 31.0 | 214 | 0.3 |
| 90/10 | 29.7 | 205 | 28.6 | 197 | 3.7 |
| 80/20 | 28.1 | 194 | 25.9 | 179 | 7.8 |
| 75/25 | 27.2 | 188 | 24.6 | 170 | 9.6 |
| 74/26 | 27.1 | 187 | 24.3 | 168 | 10.3 |
| HFC-161/butane (−20° C.) | | | | | |
| 99/1 | 31.1 | 214 | 31.0 | 214 | 0.3 |
| 90/10 | 29.8 | 205 | 29.1 | 201 | 2.3 |
| 80/20 | 28.4 | 196 | 26.9 | 185 | 5.3 |
| 70/30 | 26.9 | 185 | 24.6 | 170 | 8.6 |
| 67/33 | 26.5 | 183 | 23.9 | 165 | 9.8 |
| 66/34 | 26.3 | 181 | 23.6 | 163 | 10.3 |
| HFC-161/isobutane (−20° C.) | | | | | |
| 99/1 | 31.2 | 215 | 31.2 | 215 | 0.0 |
| 90/10 | 30.5 | 210 | 30.3 | 209 | 0.7 |
| 80/20 | 29.6 | 204 | 29.0 | 200 | 2.0 |
| 70/30 | 28.6 | 197 | 27.5 | 190 | 3.8 |
| 60/40 | 27.4 | 189 | 25.6 | 177 | 6.6 |
| 52/48 | 26.4 | 182 | 23.9 | 165 | 9.5 |
| 51/49 | 26.3 | 181 | 23.6 | 163 | 10.3 |
| HFC-161/DME (−30° C.) | | | | | |
| 1/99 | 11.6 | 80.0 | 11.6 | 80.0 | 0.0 |
| 10/90 | 12.4 | 85.5 | 12.1 | 83.4 | 2.4 |
| 20/80 | 13.2 | 91.0 | 12.7 | 87.6 | 3.8 |
| 30/70 | 14.1 | 97.2 | 13.3 | 91.7 | 5.7 |
| 40/60 | 15.0 | 103 | 14.1 | 97.2 | 6.0 |
| 50/50 | 16.0 | 110 | 15.0 | 103 | 6.3 |
| 60/40 | 17.0 | 117 | 16.0 | 110 | 5.9 |
| 70/30 | 17.9 | 123 | 17.1 | 118 | 4.5 |
| 80/20 | 18.9 | 130 | 18.3 | 126 | 3.2 |
| 90/10 | 19.9 | 137 | 19.6 | 135 | 1.5 |
| 99/1 | 20.8 | 143 | 20.8 | 143 | 0.0 |
| HFC-281ea/HFC-134a (−10° C.) | | | | | |
| 1/99 | 29.1 | 201 | 29.0 | 200 | 0.3 |
| 10/90 | 26.7 | 184 | 25.6 | 177 | 4.1 |
| 20/80 | 24.4 | 168 | 22.7 | 157 | 7.0 |
| 30/70 | 22.4 | 154 | 20.4 | 141 | 8.9 |

|  | INITIAL | | 50% LEAK | | |
|---|---|---|---|---|---|
| WT % A/WT % B | PSIA | KPA | PSIA | KPA | DELTA % P |
| 40/60 | 20.6 | 142 | 18.8 | 130 | 8.7 |
| 50/50 | 19.1 | 132 | 17.5 | 121 | 8.4 |
| 60/40 | 17.8 | 123 | 16.5 | 114 | 7.3 |
| 70/30 | 16.7 | 115 | 15.8 | 109 | 5.4 |
| 80/20 | 15.7 | 108 | 15.1 | 104 | 3.8 |
| 90/10 | 14.9 | 103 | 14.6 | 101 | 2.0 |
| 99/1 | 14.2 | 97.9 | 14.2 | 97.9 | 0.0 |
| HFC-281ea/HFC-152a (−20° C.) | | | | | |
| 1/99 | 17.8 | 123 | 17.8 | 123 | 0.0 |
| 10/90 | 17.0 | 117 | 16.6 | 114 | 2.4 |
| 20/80 | 16.0 | 110 | 15.3 | 105 | 4.4 |
| 30/70 | 15.1 | 104 | 14.2 | 97.9 | 6.0 |
| 40/60 | 14.2 | 97.9 | 13.2 | 91.0 | 7.0 |
| 50/50 | 13.3 | 91.7 | 12.3 | 84.8 | 7.5 |
| 60/40 | 12.4 | 85.5 | 11.6 | 80.0 | 6.5 |
| 70/30 | 11.6 | 80.0 | 10.9 | 75.2 | 6.0 |
| 80/20 | 10.8 | 74.5 | 10.2 | 70.3 | 5.6 |
| 90/10 | 10.0 | 68.9 | 9.68 | 66.7 | 3.2 |
| 99/1 | 9.28 | 64.0 | 9.23 | 63.6 | 0.5 |
| HFC-281ea/HFC-3-10-1sy (0° C.) | | | | | |
| 99/1 | 21.0 | 145 | 20.9 | 144 | 0.5 |
| 90/10 | 20.3 | 140 | 20.1 | 139 | 1.0 |
| 80/20 | 19.6 | 135 | 19.1 | 132 | 2.6 |
| 70/30 | 18.8 | 130 | 18.0 | 124 | 4.3 |
| 60/40 | 17.9 | 123 | 16.9 | 117 | 5.6 |
| 50/50 | 17.0 | 117 | 15.7 | 108 | 7.6 |
| 41/59 | 16.1 | 111 | 14.5 | 100 | 9.9 |
| 40/60 | 16.0 | 110 | 14.3 | 98.6 | 10.6 |
| HFC-281ea/propane (−10° C.) | | | | | |
| 1/99 | 35.3 | 344 | 49.8 | 343 | 0.2 |
| 10/90 | 48.6 | 335 | 48.1 | 332 | 1.0 |
| 20/80 | 47.1 | 325 | 45.7 | 315 | 3.0 |
| 30/70 | 45.4 | 313 | 42.9 | 296 | 5.5 |
| 40/60 | 43.4 | 299 | 39.3 | 271 | 9.4 |
| 41/59 | 43.2 | 298 | 38.9 | 268 | 10.0 |
| HFC-281ea/DME (−9.95° C.) | | | | | |
| 1/99 | 26.7 | 184 | 26.7 | 184 | 0.0 |
| 10/90 | 25.8 | 178 | 25.4 | 175 | 1.6 |
| 20/80 | 24.8 | 171 | 24.1 | 166 | 2.8 |
| 30/70 | 23.7 | 163 | 22.7 | 157 | 4.2 |
| 40/60 | 22.5 | 155 | 21.3 | 147 | 5.3 |
| 50/50 | 21.3 | 147 | 20.0 | 138 | 6.1 |
| 60/40 | 20.0 | 138 | 18.7 | 129 | 6.5 |
| 70/30 | 18.7 | 129 | 17.5 | 121 | 6.4 |
| 80/20 | 17.3 | 119 | 16.3 | 112 | 5.8 |
| 90/10 | 15.9 | 110 | 15.2 | 105 | 4.4 |
| 99/1 | 14.4 | 99.3 | 14.3 | 98.6 | 0.7 |
| HFC-3-10-1sy/HFC-134 (−21.7° C.) | | | | | |
| 13.9/86.1 | 14.7 | 101.4 | 14.7 | 101.4 | 0.0 |
| 7/93 | 14.5 | 100.0 | 14.3 | 98.6 | 1.4 |
| 1/99 | 13.7 | 94.5 | 13.5 | 93.1 | 1.5 |
| 0/100 | 13.4 | 92.4 | 13.4 | 92.4 | 0.0 |
| 20/80 | 14.6 | 100.7 | 14.6 | 100.7 | 0.0 |
| 30/70 | 14.5 | 100.0 | 14.2 | 97.9 | 2.1 |
| 40/60 | 14.3 | 98.6 | 13.5 | 93.1 | 5.6 |
| 44/56 | 14.2 | 97.9 | 12.8 | 88.3 | 9.9 |
| 45/55 | 14.2 | 97.9 | 12.6 | 86.9 | 11.3 |
| 100/0 | 3.89 | 26.8 | 3.89 | 26.8 | 0.0 |
| HFC-3-10-1sy/HFC-134a (0° C.) | | | | | |
| 1/99 | 42.9 | 296 | 42.9 | 296 | 0.0 |
| 5/95 | 42.3 | 292 | 42.1 | 290 | 0.5 |
| 10/90 | 41.5 | 286 | 40.8 | 281 | 1.7 |
| 15/85 | 40.6 | 280 | 39.4 | 272 | 3.0 |
| 20/80 | 39.7 | 274 | 38.0 | 262 | 4.3 |
| 25/75 | 38.9 | 268 | 36.4 | 251 | 6.4 |
| 30/70 | 38.0 | 262 | 34.7 | 239 | 8.7 |
| 32/68 | 37.7 | 260 | 34.0 | 234 | 9.8 |
| 33/67 | 37.5 | 259 | 33.6 | 232 | 10.4 |

|  | INITIAL | | 50% LEAK | | |
|---|---|---|---|---|---|
| WT % A/WT % B | PSIA | KPA | PSIA | KPA | DELTA % P |
| HFC-3-10-1sy/HFC-152a (0° C.) | | | | | |
| 1/99 | 38.4 | 265 | 38.4 | 265 | 0.0 |
| 10/90 | 36.8 | 254 | 36.0 | 248 | 2.2 |
| 20/80 | 35.0 | 241 | 33.1 | 228 | 5.4 |
| 30/70 | 33.2 | 229 | 30.0 | 207 | 9.6 |
| 31/69 | 33.0 | 228 | 29.6 | 204 | 10.3 |
| HFC-3-10-1sy/HFC-236ea (−1.7° C.) | | | | | |
| 33.6/66.4 | 14.7 | 101 | 14.7 | 101 | 0.0 |
| 20/80 | 14.5 | 100 | 14.1 | 97.0 | 2.9 |
| 11/89 | 13.8 | 94.9 | 12.4 | 85.5 | 9.9 |
| 50/50 | 14.6 | 100 | 14.3 | 98.5 | 1.9 |
| 60/40 | 14.4 | 99.3 | 13.2 | 90.7 | 8.7 |
| 61/39 | 14.4 | 99.3 | 12.9 | 88.9 | 10.4 |
| 100/0 | 8.91 | 61.4 | 8.91 | 61.4 | 0.0 |
| 0/100 | 10.4 | 71.7 | 10.4 | 71.7 | 0.0 |
| 1/99 | 11.0 | 75.6 | 10.5 | 72.3 | 4.4 |
| 3/97 | 11.9 | 81.8 | 10.7 | 73.9 | 9.7 |
| HFC-3-10-1sy/HFC-236fa (−2.5° C.) | | | | | |
| 12.7/87.3 | 14.7 | 101 | 14.7 | 101 | 0.0 |
| 1/99 | 14.2 | 98.0 | 14.2 | 97.8 | 0.2 |
| 0/100 | 14.1 | 97.2 | 14.1 | 97.2 | 0.0 |
| 40/60 | 13.9 | 95.6 | 13.2 | 91.1 | 4.7 |
| 50/50 | 13.4 | 92.1 | 12.2 | 84.0 | 8.8 |
| 52/48 | 13.2 | 91.3 | 12.0 | 82.5 | 9.7 |
| 53/47 | 13.2 | 90.9 | 11.8 | 81.6 | 10.2 |
| 100/0 | 8.64 | 59.6 | 8.64 | 59.6 | 0.0 |
| HFC-3-10-1sy/butane (0° C.) | | | | | |
| 1/99 | 14.9 | 103 | 14.9 | 103 | 0.0 |
| 10/90 | 14.6 | 101 | 14.5 | 99.8 | 0.7 |
| 20/80 | 14.2 | 97.7 | 14.0 | 96.4 | 1.3 |
| 30/70 | 13.7 | 94.7 | 13.5 | 92.7 | 2.0 |
| 40/60 | 13.3 | 91.4 | 12.9 | 88.9 | 2.7 |
| 50/50 | 12.8 | 87.9 | 12.3 | 85.1 | 3.2 |
| 60/40 | 12.2 | 84.1 | 11.8 | 81.1 | 3.6 |
| 70/30 | 11.6 | 80.0 | 11.2 | 77.1 | 3.7 |
| 80/20 | 11.0 | 75.6 | 10.6 | 73.1 | 3.4 |
| 90/10 | 10.3 | 70.8 | 10.0 | 69.2 | 2.2 |
| 99/1 | 9.59 | 66.1 | 9.56 | 65.9 | 0.3 |
| HFC-3-10-1sy/isobutane (0° C.) | | | | | |
| 1/99 | 22.6 | 156 | 22.6 | 156 | 0.0 |
| 10/90 | 21.7 | 150 | 21.3 | 147 | 2.1 |
| 20/80 | 20.7 | 143 | 19.8 | 136 | 4.3 |
| 30/70 | 19.6 | 135 | 18.3 | 126 | 6.5 |
| 40/60 | 18.4 | 127 | 16.8 | 116 | 8.8 |
| 45/55 | 17.8 | 123 | 16.0 | 111 | 9.9 |
| 46/54 | 17.7 | 122 | 15.9 | 110 | 10.1 |
| 88/12 | 11.6 | 80.2 | 10.5 | 72.1 | 10.1 |
| 89/11 | 11.5 | 79.0 | 10.4 | 71.5 | 9.5 |
| 99/1 | 9.69 | 66.8 | 9.57 | 66.0 | 1.2 |
| HFC-3-10-1sy/propane (−20° C.) | | | | | |
| 1/99 | 35.2 | 243 | 35.0 | 241 | 0.6 |
| 10/90 | 33.5 | 231 | 31.9 | 220 | 4.8 |
| 19/81 | 31.6 | 218 | 28.6 | 197 | 9.5 |
| 20/80 | 31.4 | 216 | 28.2 | 194 | 10.2 |
| HFC-3-10-1sy/DME (−10° C.) | | | | | |
| 1/99 | 26.7 | 184 | 26.7 | 184 | 0.0 |
| 10/90 | 26.0 | 179 | 25.7 | 177 | 1.2 |
| 20/80 | 25.1 | 173 | 24.4 | 168 | 2.8 |
| 30/70 | 24.2 | 167 | 22.9 | 158 | 5.4 |
| 40/60 | 23.2 | 160 | 21.1 | 145 | 9.1 |
| 42/58 | 23.0 | 159 | 20.7 | 143 | 10.0 |
| 43/57 | 22.8 | 157 | 20.5 | 141 | 10.1 |

The results of this Example show that these compositions are azeotropic or azeotrope-like because when 50 wt. % of an original composition is removed, the vapor pressure of the remaining composition is within about 10% of the vapor pressure of the original composition, at a temperature of 25° C.

EXAMPLE 3

Impact of Vapor Leakage at −20° C.

A leak test is performed on compositions of HFC-3-10-1sy and HFC-236fa, at the temperature of −20° C. The results are summarized below. "A" represents HFC-3-10-1sy and "B" represents HFC-236fa.

| | INITIAL | | 50% LEAK | | |
|---|---|---|---|---|---|
| WT % A/WT % B | PSIA | KPA | PSIA | KPA | DELTA % P |
| HFC-3-10-1sy/HFC-236fa | | | | | |
| 16.3/83.7 | 6.86 | 47.3 | 6.86 | 47.3 | 0.0 |
| 10/90 | 6.82 | 47.0 | 6.80 | 46.9 | 0.3 |
| 1/99 | 6.49 | 44.7 | 6.47 | 44.6 | 0.3 |
| 30/70 | 6.75 | 46.5 | 6.66 | 45.9 | 1.3 |
| 40/60 | 6.59 | 45.4 | 6.34 | 43.7 | 3.8 |
| 50/50 | 6.37 | 43.9 | 5.90 | 40.7 | 7.4 |
| 55/45 | 6.25 | 43.1 | 5.63 | 38.8 | 9.9 |
| 56/44 | 6.22 | 42.9 | 5.58 | 38.5 | 10.3 |

These results show that compositions of HFC-3-10-1sy and HFC-236fa are azeotropic or azeotrope-like at different temperatures, but that the weight percents of the components vary as the temperature is changed.

EXAMPLE 4

Vapor Pressures and Kauri-Butanol Values

Vapor pressures of the compounds of the present invention are given below. The data indicate these compounds are useful replacements for hydrocarbons widely used in aerosol formulations today. HFC-281ea and isobutane as well as HFC-161 and propane have nearly identical vapor pressures. Kauri-butanol values for the compounds of the present invention are also higher than each respective hydrocarbon. This indicates these compounds have better solvent capability as well as compatibility with aerosol resins and other active ingredients.

| | Vapor Pressure (Psig) | | Kauri-Butanol |
|---|---|---|---|
| | 70° F. | 130° F. | Value |
| HFC-161 | 106 | 264 | 16.3 |
| HFC-281ea | 31 | 99 | 20.3 |
| HFC-3-10-1sy | 5 | 38 | — |
| Propane | 108 | 262 | 15 |
| Isobutane | 31 | 97 | 18 |
| Butane | 17 | 65 | 20 |

EXAMPLE 5

VOC (Volatile Organic Compound) Predictions

Kinetic rate measurements were measured experimentally (Jet Propulsion Laboratories) or predicted for compounds of the present invention using group reactivity methodology of R. Atkinson (ref: Kwok, E. S. C., and R. Atkinson, "Estimation of Hydroxyl Radical Reaction Rate Constants for Gas-Phase Organic Compounds using a Structure-Reactivity Relationship: An Update", Final Report to CMA Contract No. ARC-8.0-OR, 1994). A compound can be considered a potential non-VOC if its kinetic rate at 298 degrees K relative to ethane is less than 1.0. Results are shown in the Table below.

TABLE

| Compound | k at 298K $cm^3$/molecule-sec for OH radical reaction | k relative to ethane | Measured or predicted |
|---|---|---|---|
| Ethane | $2.4 \times 10^{-13}$ | 1.0 | Measured |
| Propane | $1.1 \times 10^{-12}$ | 4.6 | Measured |
| Butane | $2.54 \times 10^{-12}$ | 10.5 | Predicted |
| Isobutane | $2.33 \times 10^{-12}$ | 9.7 | Predicted |
| HFC-161 | $1.7 \times 10^{-13}$ | 0.7 | Measured |
| HFC-281ea | $4.6 \times 10^{-13}$ | 1.9 | Measured |
| HFC-3-10-1sy | $7.7 \times 10-14$ | 0.3 | Predicted |

The compounds of the present invention have significantly reduced photochemical (hydroxyl radical) reactivity compared to hydrocarbons propane, butane and isobutane widely used in aerosols today. Using the compounds of the present invention in aerosols can significantly reduce ground level smog. HFC-161 and HFC-3-10-1sy could be classified as non-VOCs because their reactivity is less than ethane. And HFC-281ea is significantly less reactive than its hydrocarbon analogue isobutane.

EXAMPLE 6

55% VOC Hair Spray Prototype

A 55% VOC (volatile organic compound) hair spray in accordance with the present invention is formulated as follows:

TABLE

| | Wt % |
|---|---|
| Octylacrylamide/acrlyates/butylaminoethyl methacrylate copolymer (National Starch) | 5.00 |
| AMP (2-amino-2-methyl-1-propanol, Kodak) | 0.96 |
| Dimethicone silylate (Hydrolabs) | 0.50 |
| Water | 3.54 |

To this mixture is added ethanol and propellants of the present invention to yield a 55% VOC formulation:

| | Wt %/Wt % | Wt % Ethanol |
|---|---|---|
| HFC-161 | 35.00 | 55.00 |
| HFC-3-10-1sy | 35.00 | 55.00 |
| HFC-161/HFC-134a | 5.00/30.00 | 55.00 |
| HFC-161/HFC-152a | 5.00/30.00 | 55.00 |
| HFC-161/HFC-281ea | 35.00/7.00 | 48.00 |
| HFC-161/HFC-3-10-1sy | 28.00/7.00 | 55.00 |
| HFC-281ea/HFC-134a | 7.00/35.00 | 48.00 |
| HFC-281ea/HFC-152a | 7.00/35.00 | 48.00 |
| HFC-281ea/HFC-3-10-1sy | 7.00/35.00 | 48.00 |
| HFC-3-10-1sy/HFC-134 | 5.00/30.00 | 55.00 |
| HFC-3-10-1sy/HFC-134a | 5.00/30.00 | 55.00 |
| HFC-3-10-1sy/HFC-152a | 7.00/28.00 | 55.00 |

The vapor pressure of each mixture may vary with formulation. This example is illustrative and does not reflect an optimized system.

EXAMPLE 7

55% VOC Hair Spray Prototype

Two 55% VOC hair sprays in accordance with the present invention are formulated as follows:

| Component | A Wt % | B Wt % |
|---|---|---|
| PVM/MA Copolymer | 6.00 | 6.00 |
| AMP | 0.35 | 0.35 |
| Water | 29.05 | 38.65 |
| Ethanol 40-1 | 34.60 | 25.00 |

To these mixtures are added 30.00 weight percent of one of the following compositions of the present invention to yield a 55% VOC formulation:

TABLE

| | Formulation | |
|---|---|---|
| Component | A Wt % | B Wt % |
| HFC-161/DME | 9.60/20.40 | — |
| HFC-161/butane | 9.60/20.40 | — |
| HFC-161/isobutane | 9.60/20.40 | — |
| HFC-281ea/propane | — | 9.60/20.40 |
| HFC-281ea/DME | — | 9.60/20.40 |
| HFC-3-10-1sy/butane | 9.60/20.40 | — |
| HFC-3-10-1sy/isobutane | 9.60/20.40 | — |
| HFC-3-10-1sy/propane | 9.60/20.40 | — |
| HFC-3-10-1sy/DME | 9.60/20.40 | — |

The vapor pressure of each mixture may vary with formulation. This example is illustrative and does not reflect an optimized system. The formulations containing HFC-281ea will have less impact on ground level smog than those containing hydrocarbons because HFC-281ea has less significantly less photochemical reactivity.

EXAMPLE 8

Fragrance Prototype

A fragrance in accordance with the present invention is formulated as follows:

TABLE

| | Wt % |
|---|---|
| Fragrance | 3.0 |
| Ethanol 40-1 | 70.0 |
| Water | 15.0 |

To this mixture is added 12.0 weight percent of one of the following mixtures of the present invention:

| | Wt % | % VOC |
|---|---|---|
| HFC-161 | 12.0 | 70 |
| HFC-281ea | 12.0 | 82 |
| HFC-3-10-1sy | 12.0 | 70 |
| HFC-161/HFC-134a | 3.0/9.0 | 70 |
| HFC-161/HFC-152a | 3.0/9.0 | 70 |
| HFC-161/HFC-281ea | 9.0/3.0 | 73 |
| HFC-161/HFC-3-10-1sy | 9.0/3.0 | 70 |
| HFC-161/butane | 9.0/3.0 | 73 |
| HFC-161/isobutane | 9.0/3.0 | 73 |
| HFC-161/DME | 6.0/6.0 | 76 |
| HFC-281ea/HFC-134a | 3.0/9.0 | 73 |
| HFC-281ea/HFC-152a | 3.0/9.0 | 73 |
| HFC-281ea/HFC-3-10-1sy | 3.0/9.0 | 73 |
| HFC-281ea/propane | 3.0/9.0 | 82 |
| HFC-281ea/DME | 3.0/9.0 | 82 |
| HFC-3-10-1sy/HFC-134 | 2.0/10.0 | 70 |
| HFC-3-10-1sy/HFC-134a | 3.0/9.0 | 70 |
| HFC-3-10-1sy/HFC-152a | 3.0/9.0 | 70 |
| HFC-3-10-1sy/butane | 5.0/4.0 | 74 |
| HFC-3-10-1sy/isobutane | 4.0/5.0 | 75 |
| HFC-3-10-1sy/propane | 2.0/10.0 | 80 |
| HFC-3-10-1sy/DME | 3.0/9.0 | 79 |

The vapor pressure of each mixture may vary with formulation. This example is illustrative and does not reflect an optimized system. The formulations containing HFC-281ea will have less impact on ground level smog than those containing hydrocarbons because HFC-281ea has less significantly less photochemical reactivity.

EXAMPLE 9

Aerosol Antiperspirant Prototype

A 60% VOC aerosol antiperspirant in accordance with the present invention is formulated as follows:

TABLE

| | Wt % |
|---|---|
| Aluminum chlorohydrate | 10.0 |
| Isopropyl myristate | 6.0 |
| Silicone fluid DC-344 (Dow Corning) | 6.0 |
| Talc | 0.5 |
| Quaternium-18 hectorite | 0.5 |
| Ethanol 40-1 | 2.0 |

To this mixture is added 75.0 weight percent of one of the following mixtures of the present invention to yield a 60% VOC formulation:

| HFC-161/DME | 17.0/58.0 |
|---|---|
| HFC-161/butane | 17.0/58.0 |
| HFC-161/isobutane | 17.0/58.0 |
| HFC-3-10-1sy/butane | 17.0/58.0 |
| HFC-3-10-1sy/isobutane | 17.0/58.0 |
| HFC-3-10-1sy/propane | 17.0/58.0 |
| HFC-3-10-1sy/DME | 17.0/58.0 |

Similar formulations can also be developed for air fresheners, household disinfectants, insect foggers and spray paints using the compositions of the present invention.

EXAMPLE 10

Hair Spray Performance

The following example demonstrates efficacy of the patent invention in hair sprays, compared to a widely used hydrofluorocarbon propellant HFC-152a ($CH_3CHF_2$) as shown in the table below. The formulations were one phase indicating complete miscibility. Tack and dry times, curl droop, and flame extension tests were used to evaluate performance. Curl droop measures the percent lengthening of a curl five minutes after spraying. Flame extension was measured to determine the flammability of each formulation. Results show each formulation achieved 80% or higher curl retention, good tack and dry times, and acceptable flame extensions despite the fact that the formulations were not optimized.

TABLE

| Component | Formulation | | | | | | | |
|---|---|---|---|---|---|---|---|---|
| (Wt %) | A | B | C | D | E | F | G | H |
| Resin* | 25 | 25 | 25 | 25 | 25 | 19.5 | 19.5 | 19.5 |
| Ethanol | 43 | 43 | 43 | 43 | 43 | 35.0 | 35.0 | 35.0 |
| Additives | 2 | 2 | 2 | 2 | 2 | 1.7 | 1.7 | 1.7 |
| HFC-161 | — | 30 | — | 18 | — | — | — | 10.0 |
| HFC-281ea | — | — | 30 | — | 12 | — | 10.0 | — |
| HFC-152a | 30 | — | — | — | 18 | 10.0 | — | — |
| Butane | — | — | — | 12 | — | — | — | — |
| Water | — | — | — | — | — | 13.8 | 13.8 | 13.8 |
| DME | — | — | — | — | — | 20.0 | 20.0 | 20.0 |
| Total Wt % | 100 | 100 | 100 | 100 | 100 | 100 | 100 | 100 |
| Vapor Pressure @ 70° F. (psig) | 60 | 95 | 31 | 79 | 52 | 47 | 40 | 64 |
| % VOC | 43 | 43 | 73 | 55 | 55 | 55 | 65 | 55 |
| Curl droop % | 9 | 21 | 11 | 17 | 16 | 18 | 11 | 17 |
| Tack Time (sec) | 10 | 14 | 4 | 7 | 11 | 8 | 14 | 58 |
| Dry Time (sec) | 24 | 28 | 17 | 46 | 54 | 21 | 39 | 73 |
| Flame Extension (inches) | 4 | 6 | 9 | 4 | 13 | 4 | 12 | 16 |

*t-butylacrylate/ethylacrylate/methacrylic acid copolymer resin

EXAMPLE 11

Air Freshener Performance

To test air freshener flammability and miscibility, compositions of the present invention were formulated into air fresheners as shown in the table below. The formulations were one phase indicating complete miscibility. Flame extensions were measured which were less than 18 inches, the desirable maximum. The formulations showed good spray patterns and delivery.

TABLE

| | Formulation | |
|---|---|---|
| Component | A Wt % | B Wt % |
| Fragrance | 1 | 1 |
| Water | 4 | 4 |
| Ethanol | 30 | 30 |
| HFC-161 | 65 | — |
| HFC-281ea | — | 65 |
| Total Wt % | 100 | 100 |
| Vapor Pressure @ 70 F. (psig) | 106 | 33 |
| Flame Extension (in) | 13 | 16 |

EXAMPLE 12

Fragrance Performance

To test fragrance flammability and miscibility, compositions of the present invention were formulated into fragrances as shown in the table below. The formulations were one phase indicating complete miscibility. Flame extensions were then measured which were less than 18 inches, the desirable maximum. The formulations showed good spray patterns and delivery.

TABLE

| | Formulation | |
|---|---|---|
| Component | A Wt % | B Wt % |
| Fragrance | 3 | 3 |
| Ethanol | 70 | 70 |
| Water | 15 | 15 |
| HFC-161 | 12 | — |
| HFC-281ea | — | 12 |
| | 100 | 100 |
| Vapor Pressure @ 70 F. (psig) | 46 | 14 |
| Flame Extension (in) | 13 | 10 |

EXAMPLE 13

Shelf Life Stability

Compositions shown in the table below were prepared and loaded into tin-plate aerosol cans. Cans were placed in an oven at 120° F. or held at room temperature (21–23° C.) for several months.

TABLE

| Composition | Temperature | Time | Can Interior |
|---|---|---|---|
| HFC-161/Ethanol (30/70 wt %) | 120° F. | 2 months | No corrosion Slight detinning |
| | | 6 months | No corrosion Medium detinning |
| FC-161/Ethanol (30/70 wt %) | Room | 24 months | No corrosion Slight detinning |
| HFC-281ea/Ethanol (60/40 wt %) | 120° F. | 1 month | No corrosion or detinning |
| | | 3 months | No corrosion or detinning |
| HFC-281ea/Ethanol/ Water (40/54/6 wt %) | 120° F. | 1 month | No corrosion or detinning |

As shown in the table, the propellant compositions demonstrated good stability in formulation solvents, even without corrosion inhibitors.

EXAMPLE 14

The following table shows the performance of various refrigerants. The data is based on the following conditions.

| | |
|---|---|
| Evaporator temperature | 45.0° F. (7.2° C.) |
| Condenser temperature | 130.0° F. (54.4° C.) |
| Subcooled | 15.0° F. (8.3° C.) |
| Return gas | 65.0° F. (18.3° C.) |
| Compressor efficiency is 75%. | |

The refrigeration capacity is based on a compressor with a fixed displacement of 3.5 cubic feet per minute and 75% volumetric efficiency. Capacity is intended to mean the change in enthalpy of the refrigerant in the evaporator per pound of refrigerant circulated, i.e. the heat removed by the refrigerant in the evaporator per time. Coefficient of performance (COP) is intended to mean the ratio of the capacity to compressor work. It is a measure of refrigerant energy efficiency.

| Refrig Comp. | Evap Press Psia | (kPa) | Cond Press Psia | (kPa) | Comp. Dis Temp. °F. | (°C.) | COP | Capacity BTU/min | (kW) |
|---|---|---|---|---|---|---|---|---|---|
| HFC-161/HFC-134a | | | | | | | | | |
| 1/99 | 55 | 379 | 215 | 1482 | 171 | 77 | 3.43 | 225 | 4.0 |
| 99/1 | 80 | 552 | 279 | 1924 | 201 | 94 | 3.49 | 316 | 5.6 |
| HFC-161/HFC-152a | | | | | | | | | |
| 1/99 | 51 | 352 | 194 | 1338 | 204 | 96 | 3.60 | 224 | 3.9 |
| 99/1 | 90 | 552 | 278 | 1917 | 200 | 93 | 3.53 | 318 | 5.6 |
| HFC-161/HFC-281ea | | | | | | | | | |
| 1/99 | 27 | 186 | 106 | 731 | 168 | 76 | 3.71 | 123 | 2.2 |
| 99/1 | 79 | 545 | 278 | 1917 | 201 | 94 | 3.49 | 314 | 5.5 |
| HFC-161/HFC-3-10-1sy | | | | | | | | | |
| 1/99 | 13 | 90 | 55 | 379 | 48 | 64 | 3.75 | 63 | 1.1 |
| 99/1 | 79 | 545 | 277 | 1910 | 201 | 94 | 3.50 | 314 | 5.5 |
| HFC-161/butane | | | | | | | | | |
| 1/99 | 20 | 138 | 82 | 565 | 155 | 68 | 3.68 | 93 | 1.6 |
| 99/1 | 79 | 545 | 277 | 1910 | 201 | 94 | 3.49 | 314 | 5.5 |
| HFC-161/isobutane | | | | | | | | | |
| 1/99 | 30 | 207 | 65 | 448 | 112 | 44 | 3.57 | 123 | 2.2 |
| 99/1 | 79 | 545 | 279 | 1924 | 201 | 94 | 3.49 | 315 | 5.5 |
| HFC-161/DME | | | | | | | | | |
| 1/99 | 49 | 338 | 183 | 1262 | 194 | 90 | 3.67 | 215 | 3.8 |
| 99/1 | 79 | 545 | 279 | 1924 | 201 | 94 | 3.49 | 315 | 5.5 |
| HFC-218ea/HFC-134a | | | | | | | | | |
| 1/99 | 54 | 372 | 212 | 1462 | 171 | 77 | 3.43 | 222 | 3.9 |
| 99/1 | 27 | 186 | 105 | 724 | 168 | 76 | 3.70 | 121 | 2.1 |
| HFC-281ea/HFC-152a | | | | | | | | | |
| 1/99 | 50 | 345 | 192 | 1324 | 204 | 95 | 3.61 | 222 | 3.9 |
| 99/1 | 27 | 186 | 105 | 724 | 168 | 76 | 3.70 | 122 | 2.1 |
| HFC-281ea/HFC-3-10-1sy | | | | | | | | | |
| 1/99 | 12 | 83 | 54 | 372 | 148 | 64 | 3.68 | 59 | 1.0 |
| 99/1 | 26 | 179 | 104 | 717 | 168 | 76 | 3.70 | 120 | 2.1 |
| HFC-281ea/propane | | | | | | | | | |
| 1/99 | 83 | 572 | 270 | 1862 | 166 | 74 | 3.32 | 282 | 5.0 |
| 99/1 | 27 | 186 | 107 | 738 | 168 | 76 | 3.71 | 123 | 2.2 |
| HFC-281ea/DME | | | | | | | | | |
| 1/99 | 48 | 331 | 181 | 1248 | 193 | 89 | 3.68 | 213 | 3.8 |
| 99/1 | 27 | 186 | 106 | 731 | 168 | 76 | 3.70 | 122 | 2.1 |
| HFC-3-10-sy/HFC-134a | | | | | | | | | |
| 1/99 | 42 | 290 | 167 | 1151 | 182 | 83 | 3.60 | 187 | 3.3 |
| 99/1 | 12 | 83 | 54 | 372 | 148 | 64 | 3.69 | 60 | 1.1 |
| HFC-3-10-1sy/HFC-134a | | | | | | | | | |
| 1/99 | 54 | 372 | 210 | 1448 | 171 | 77 | 3.44 | 221 | 3.9 |
| 99/1 | 12 | 83 | 54 | 372 | 148 | 64 | 3.69 | 60 | 1.1 |
| HFC-3-10-1sy/HFC-152a | | | | | | | | | |
| 1/99 | 50 | 345 | 191 | 1317 | 203 | 95 | 3.60 | 221 | 3.9 |
| 99/1 | 13 | 90 | 54 | 372 | 148 | 64 | 3.70 | 60 | 1.1 |
| HFC3-10-1sy/HFC-236ea | | | | | | | | | |
| 1/99 | 15 | 103 | 70 | 483 | 143 | 62 | 3.50 | 71 | 1.3 |
| 99/1 | 12 | 83 | 53 | 365 | 148 | 64 | 3.67 | 59 | 1.0 |
| HFC-3-10-1sy/HFC-236fa | | | | | | | | | |
| 1/99 | 20 | 138 | 86 | 593 | 141 | 60 | 3.42 | 86 | 1.5 |
| 99/1 | 12 | 83 | 53 | 365 | 148 | 64 | 3.67 | 59 | 1.0 |
| HFC-3-10-1sy/butane | | | | | | | | | |
| 1/99 | 19 | 131 | 80 | 552 | 155 | 68 | 3.65 | 90 | 1.6 |
| 99/1 | 12 | 83 | 53 | 365 | 148 | 64 | 3.67 | 59 | 1.0 |

-continued

| Refrig | Evap Press | | Cond Press | | Comp. Dis | | COP | Capacity BTU/min | |
|---|---|---|---|---|---|---|---|---|---|
| Comp. | Psia | (kPa) | Psia | (kPa) | Temp. °F. | (°C.) | | (kW) | |
| HFC-3-10-1sy/isobutane | | | | | | | | | |
| 1/99 | 29 | 200 | 110 | 758 | 152 | 67 | 3.56 | 120 | 2.1 |
| 99/1 | 12 | 83 | 54 | 372 | 148 | 64 | 3.68 | 59 | 1.0 |
| HFC-3-10-sy/propane | | | | | | | | | |
| 1/99 | 83 | 572 | 269 | 1855 | 166 | 74 | 3.33 | 281 | 4.9 |
| 99/1 | 13 | 90 | 55 | 379 | 147 | 64 | 3.74 | 62 | 1.1 |
| HFC-3-10-1sy/DME | | | | | | | | | |
| 1/99 | 48 | 331 | 181 | 1248 | 193 | 89 | 3.67 | 213 | 3.7 |
| 99/1 | 13 | 90 | 55 | 379 | 148 | 64 | 3.73 | 62 | 1.1 |

Additional Compounds

Other components, such as aliphatic hydrocarbons having a boiling point of −60 to +60° C., hydrofluorocarbonalkanes having a boiling point of −60 to +60° C., hydrofluoropropanes having a boiling point of between −60 to +60° C., hydrocarbon esters having a boiling point between −60 to +60° C., hydrochlorofluorocarbons having a boiling point between −60 to +60° C., hydrofluorocarbons having a boiling point of −60 to +60° C., hydrochlorocarbons having a boiling point between −60 to +60° C., chlorocarbons and perfluorinated compounds, can be added to the azeotropic or azeotrope-like compositions described above without substantially changing the properties thereof, including the constant boiling behavior, of the compositions.

Additives such as lubricants, corrosion inhibitors, surfactants, stabilizers, dyes and other appropriate materials may be added to the novel compositions of the invention for a variety of purposes provides they do not have an adverse influence on the composition for its intended application. Preferred lubricants include esters having a molecular weight greater than 250.

What is claimed is:

1. An azeotropic or azeotrope-like refrigerant composition consisting essentially of 1–99 weight percent fluoroethane and 1–99 weight percent dimethylether wherein when the temperature of said composition has been adjusted to about −30° C., said composition has a vapor pressure of about 11.6 psia (80.0 kPa) to about 20.8 psia (143 kPa).

2. A process for producing refrigeration comprising condensing a composition of claim 1 and thereafter evaporating said composition in the vicinity of a body to be cooled.

* * * * *